(12) United States Patent
Ito et al.

(10) Patent No.: US 8,861,818 B2
(45) Date of Patent: Oct. 14, 2014

(54) PREOPERATIVE PLANNING PROGRAM AND OPERATION SUPPORT JIG FOR HIP REPLACEMENT ARTHROPLASTY

(75) Inventors: Tomoyuki Ito, Niigata (JP); Ken Suda, Kashiwazaki (JP)

(73) Assignee: Lexi Corporation, Ltd., Tokyo (JP)

( * ) Notice: Subject to any disclaimer, the term of this patent is extended or adjusted under 35 U.S.C. 154(b) by 15 days.

(21) Appl. No.: 13/480,104

(22) Filed: May 24, 2012

(65) Prior Publication Data

US 2012/0230573 A1 Sep. 13, 2012

Related U.S. Application Data

(63) Continuation of application No. PCT/JP2010/070931, filed on Nov. 24, 2010.

(30) Foreign Application Priority Data

Nov. 24, 2009 (JP) .................................. 2009-266649

(51) Int. Cl.
*G06K 9/00* (2006.01)
(52) U.S. Cl.
USPC ........................................................ 382/128
(58) Field of Classification Search
CPC ... A61B 19/50; A61F 2002/4633; A61F 2/32; A61F 2/4609; A61F 2/4607; G06T 15/00; G06T 15/08; G06T 17/00; G06T 17/10
USPC ........................................................ 382/128
See application file for complete search history.

(56) References Cited

U.S. PATENT DOCUMENTS

| 5,141,512 A | 8/1992 | Farmer et al. |
| 6,711,431 B2 | 3/2004 | Sarin et al. |
| 6,991,655 B2 * | 1/2006 | Iversen ..................... 623/22.12 |
| 7,591,856 B2 * | 9/2009 | Djurivic .................... 623/22.11 |

(Continued)

FOREIGN PATENT DOCUMENTS

| CN | 2726562 Y | 9/2005 |
| JP | 2004-8707 A | 1/2004 |

(Continued)

OTHER PUBLICATIONS

International Search Report mailed by the International Searching Authority (ISA/JP) on Dec. 14, 2010 in connection with PCT International Application No. PCT/JP2010/065541, filed Sep. 9, 2010.

(Continued)

*Primary Examiner* — Tom Y Lu
(74) *Attorney, Agent, or Firm* — John P. White; Cooper & Dunham LLP

(57) ABSTRACT

According to one embodiment, a preoperative planning method performed by a computer for hip replacement arthroplasty, includes a base jig setting step of setting a three-dimensional image of a base jig having three or more columnar supports which abut on three or more reference points of the pelvis with respect to the three-dimensional image of the pelvis obtained at the image reconstruction step, and a parameter acquisition step of parameterizing and acquiring a direction of an indicator which runs through a predetermined position on the base jig in the three-dimensional image of the base jig set at the base jig setting step and becomes parallel to the installation direction of the joint prostheses determined at the joint prostheses determination step.

11 Claims, 37 Drawing Sheets

(56) References Cited

U.S. PATENT DOCUMENTS

| | | | |
|---|---|---|---|
| 7,885,705 B2 * | 2/2011 | Murphy | 600/426 |
| 8,175,683 B2 * | 5/2012 | Roose | 600/427 |
| 2004/0210233 A1 | 10/2004 | Yoon et al. | |
| 2009/0306679 A1 * | 12/2009 | Murphy | 606/130 |

FOREIGN PATENT DOCUMENTS

| | | |
|---|---|---|
| JP | 2008-188400 A | 8/2008 |
| JP | 2009-82444 A | 4/2009 |
| JP | 2009-195490 A | 9/2009 |
| WO | WO 2006/109983 | 10/2006 |
| WO | WO 2009/058319 A1 | 5/2009 |
| WO | WO 2012/007036 A1 | 1/2012 |

OTHER PUBLICATIONS

Written Opinion of the International Searching Authority mailed by the International Searching Authority (ISA/JP) on Dec. 14, 2010 in connection with PCT International Application No. PCT/JP2010/065541, filed Sep. 9, 2010.

Hagio et al. (2004). A novel system of four-dimensional motion analysis after total hip arthroplasty. *Journal of Orthopaedic Research*, 22, 665-670.

Miki et al. (2007). Anatomic hip range of motion after implantation during total hip arthroplasty as measured by a navigation system. *The Journal of Arthroplasty*, 22(7), 946-952.

Notification of Transmittal of Translation of the International Preliminary Report on Patentability (Chapter I or Chapter II), including International Preliminary Report on Patentability and Written Opinion of the International Searching Authority, mailed Jun. 21, 2012 by The International Bureau of WIPO in connection with PCT International Application No. PCT/JP2010/070931, filed Nov. 24, 2010.

Feb. 24, 2014 Chinese official action in connection with corresponding Chinese patent application no. 201080053036.6 (including English-language translation thereof).

* cited by examiner

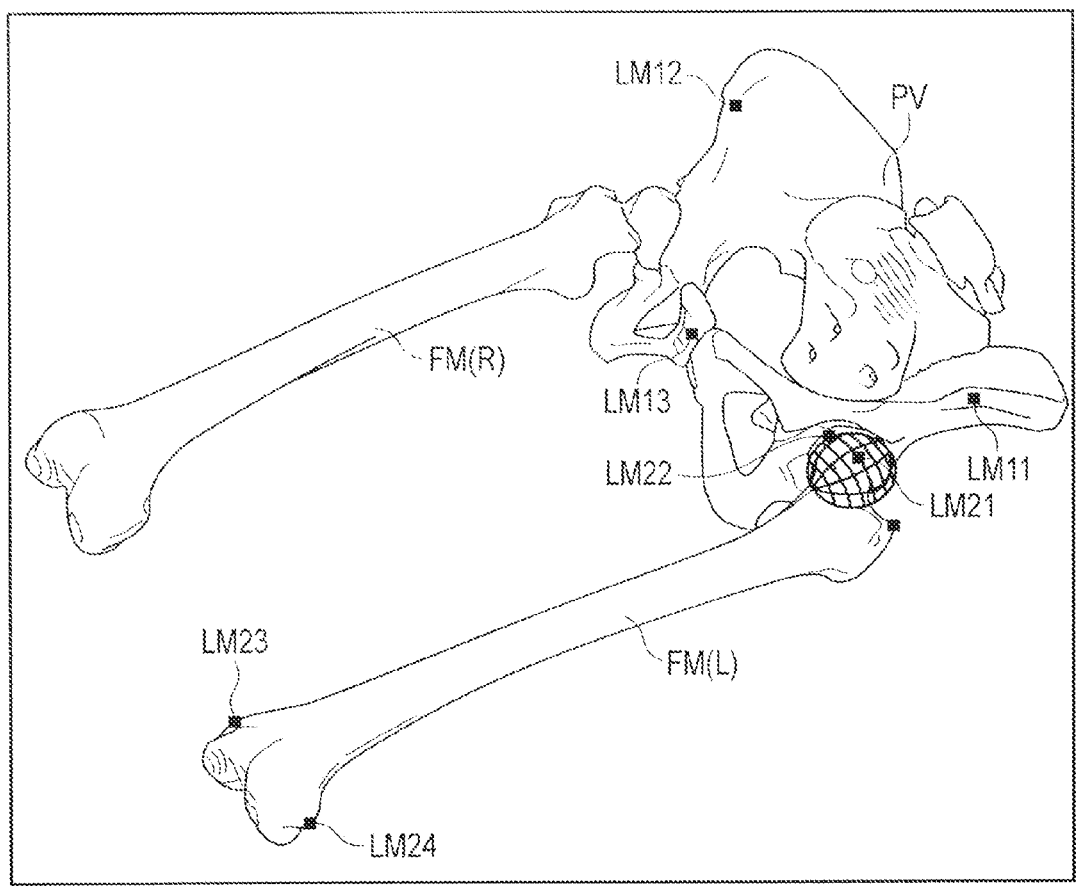
F I G. 6

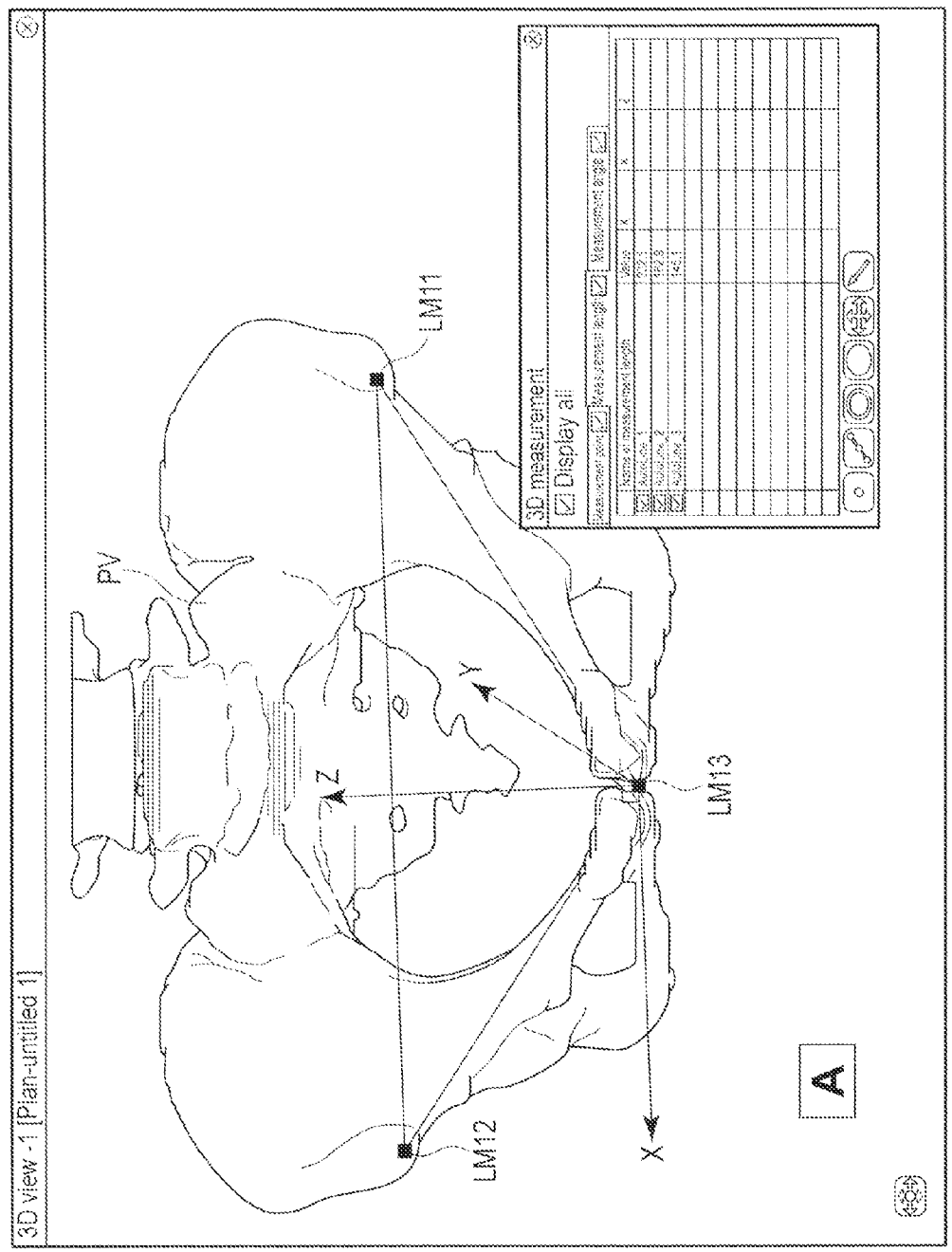
F I G. 7

| Coordinate system |
| --- |
| Pelvic coordinate system |

Selection model
| Left | Right |

Model information
| Stem | Cup | Replacement |

Lower extremity section

Movement 1.0
| Medial | Lateral |
| Anterior | Posterior |
| Proximal | Distal |

Rotation 1.0

Reduction state
☐ Apply reduction state

Alignment parameter
| Three-dimensional distance of greater trochanter | 16.50 mm |
| Leg length reduction amount | -7.30 mm |
| (W)Anterior inclination of pelvis | 7.66 Degrees |

Stem parameter
| Angle of anteversion (stem axis) | 39.93 Degrees |
| Varus-valgus | 0.00 Degrees |
| Flexion and extension | Flexion 1.00 Degrees |
| Depth | 6.11 mm |

Cup parameter
| RI | 45.00 Degrees |
| RA | 15.00 Degrees |
| OI | 43.08 Degrees |
| OA | 20.75 Degrees |

| Movement | | Rotation | |
|---|---|---|---|
| 1.0 | | 1.0 | |
| Medial | Lateral | | |
| Anterior | Posterior | | |
| Proximal | Distal | | |

Reduction state
☐ Apply reduction state

Alignment parameter
Three-dimensional distance
of greater trochanter                      13.01 mm
Leg length reduction amount           10.58 mm
(W)Anterior inclination of pelvis        9.78 Degrees Stem parameter
Angle of anteversion (stem axis) 46.29 Degrees
Varus-valgus                    Valgus 0.38 Degrees
Flexion and extension      Extension 1.36 Degrees
Depth                                              2.96 mm Cup parameter

| | | | |
|---|---|---|---|
| RI | 45.00 Degrees | | |
| RA | 23.00 Degrees | | |
| OI | 40.61 Degrees | | |
| OA | 30.98 Degrees | | |

| Movement | | Rotation | | |
|---|---|---|---|---|
| 1.0 +/− | | 1.0 +/− | | |
| Medial | Lateral | | | |
| Anterior | Posterior | | | |
| Proximal | Distal | | | |

Reduction state
☑ Apply reduction state

Alignment parameter
Three-dimensional distance
of greater trochanter          ∗11.86 mm
Leg length reduction amount    ∗13.85 mm
(W)Anterior inclination of pelvis   9.78 Degrees Stem parameter
Angle of anteversion (stem axis) 46.29 Degrees
Varus-valgus                  Valgus 0.38 Degrees
Flexion and extension   Extension 1.36 Degrees
Depth                           2.96 mm Cup parameter
| | |
|---|---|
| RI | 45.00 Degrees +/− |
| RA | 23.00 Degrees +/− |
| OI | 40.61 Degrees +/− |
| OA | 30.98 Degrees +/− |

PV
ST
CP
FM

F I G. 12

Coordinate system
Stem left

Lower extremity section
Left  Right

Selection model
Stem  Cup  Replacement

Model information

Movement
1.0
Medial | Lateral
Anterior | Posterior
Proximal | Distal

Rotation
1.0
Flexion | Extension
Varus | Valgus
Anteversion | Retrotorsion

Reduction state
☑ Apply reduction state

Alignment parameter
Three-dimensional distance of greater trochanter    ✱ 11.86 mm
Leg length reduction amount    ✱ 13.85 mm
(W)Anterior inclination of pelvis    9.78 Degrees Stem parameter
Angle of anteversion (stem axis)    46.29 Degrees
Varus-valgus    valgus 0.38 Degrees
Flexion and extension    Extension 1.36 Degrees
Depth    2.96 mm Cup parameter
RI    45.00 Degrees
RA    23.00 Degrees
OI    40.61 Degrees
OA    30.98 Degrees

F I G. 13B

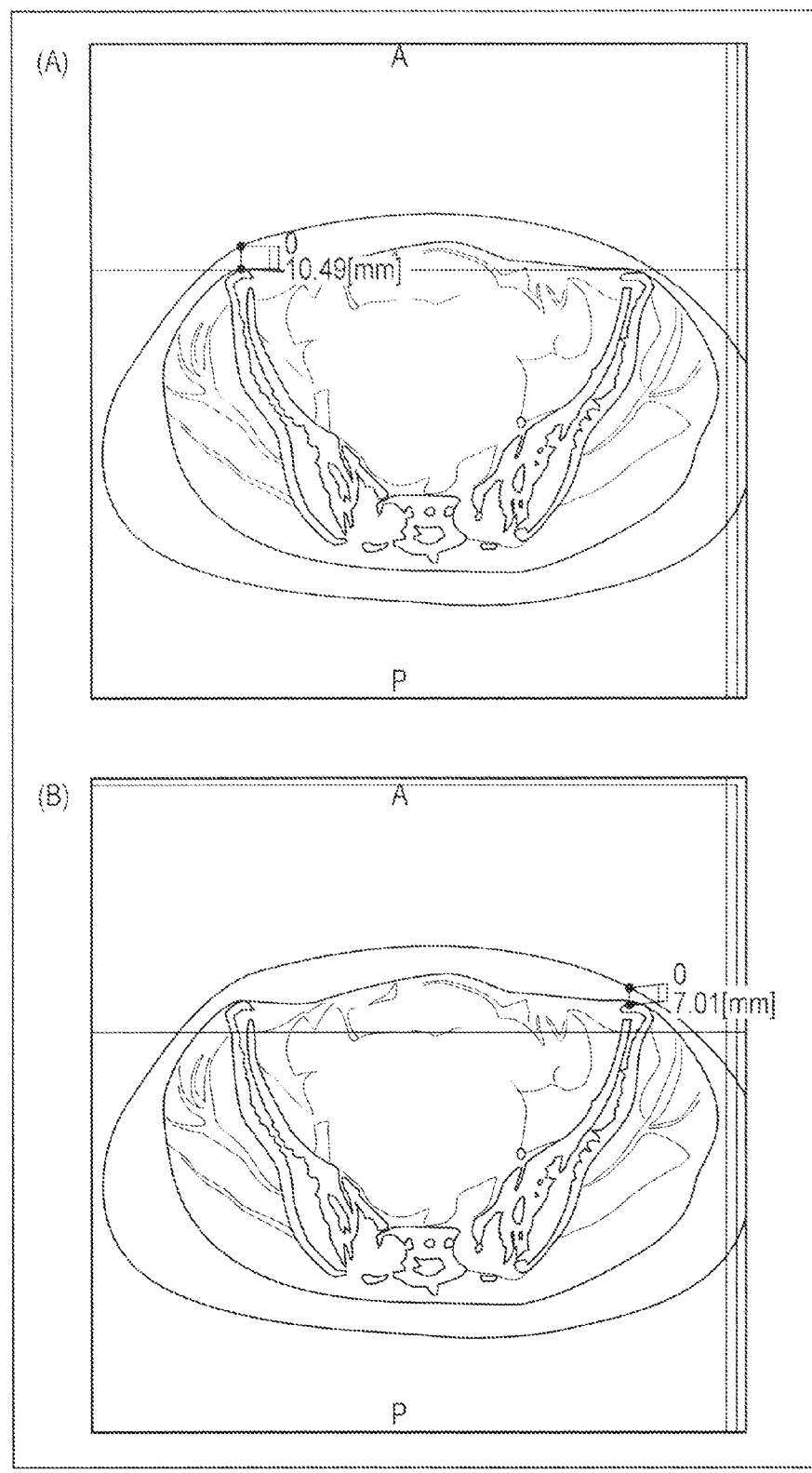
F I G. 18

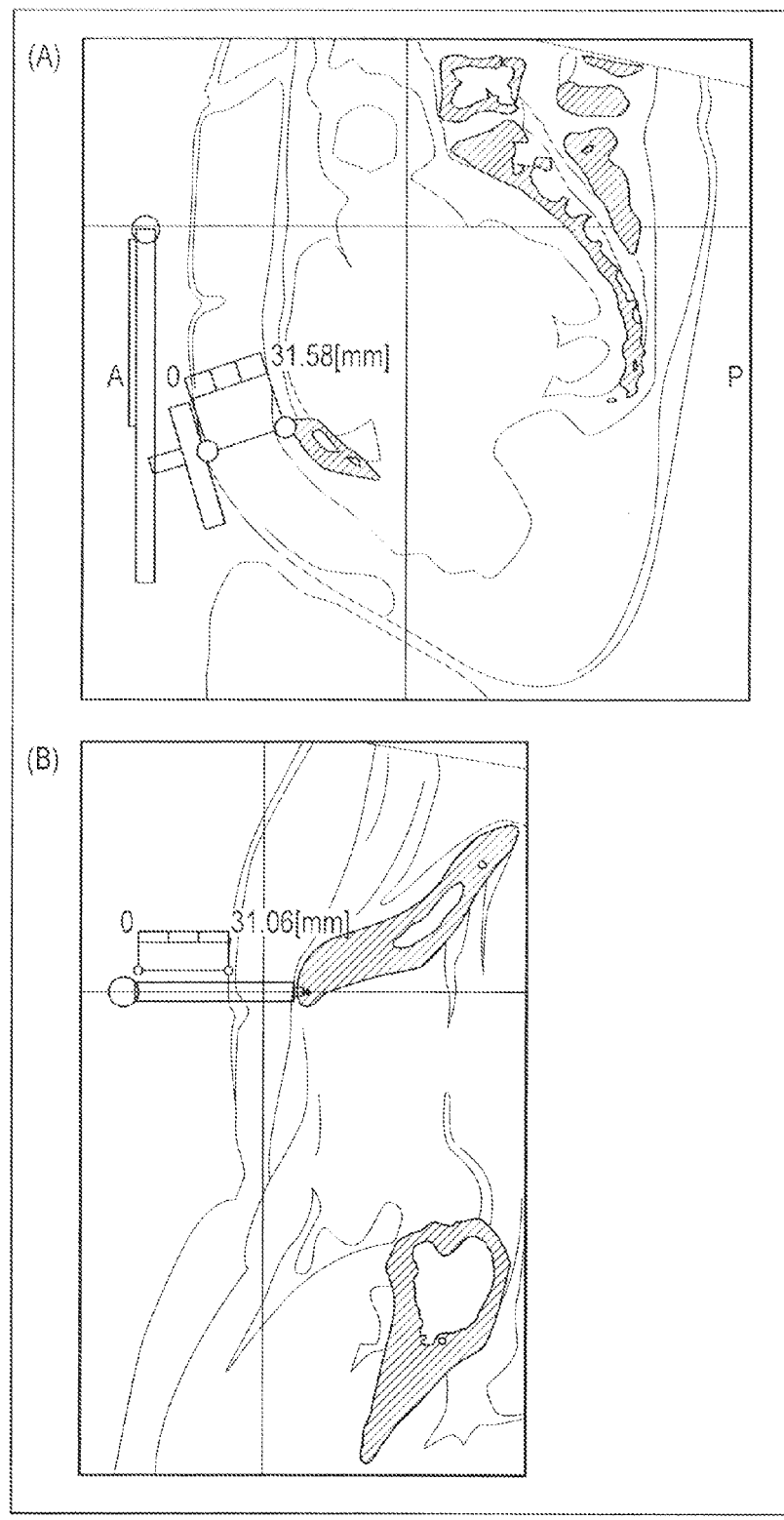
F I G. 19

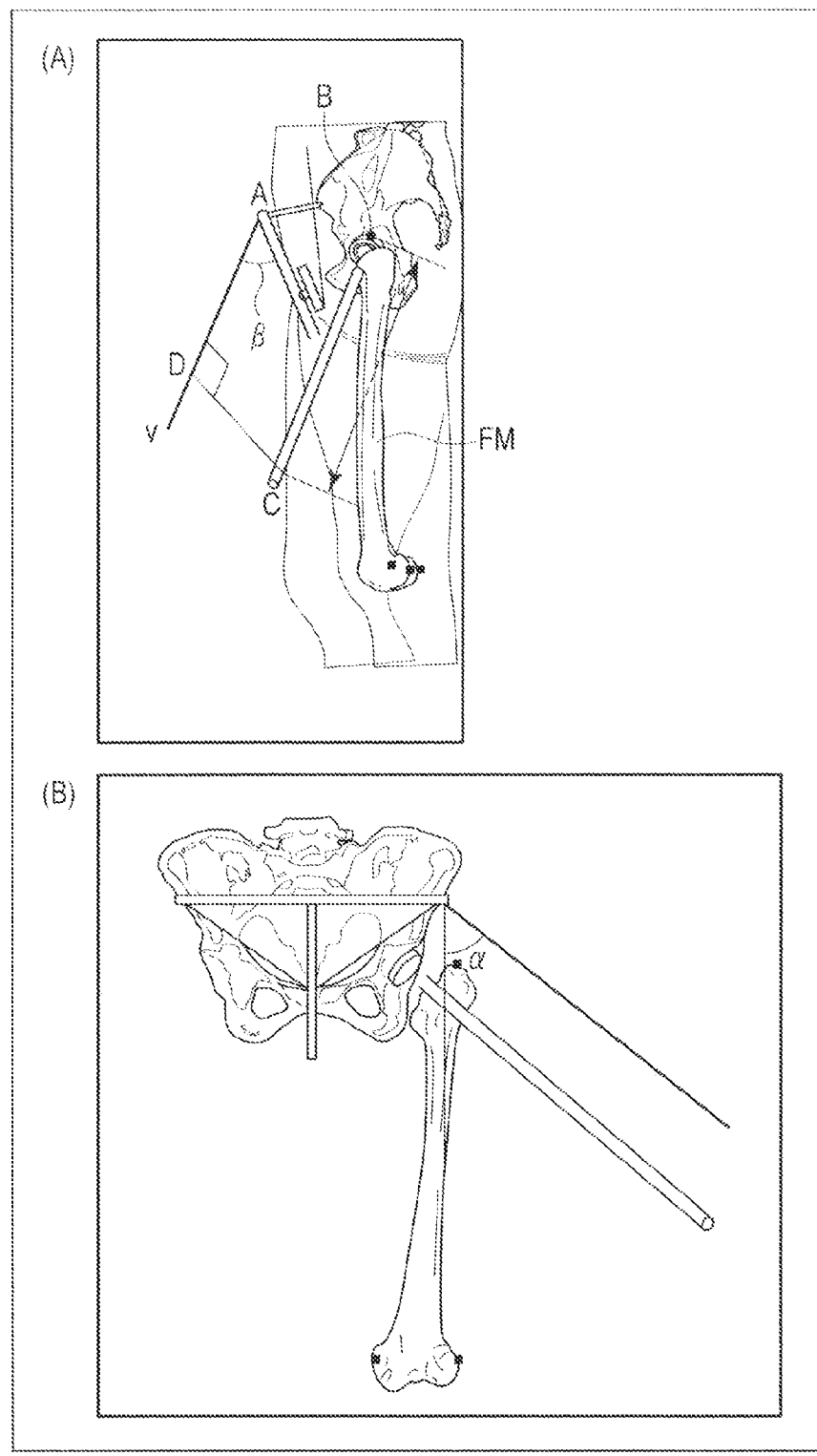
F I G. 22

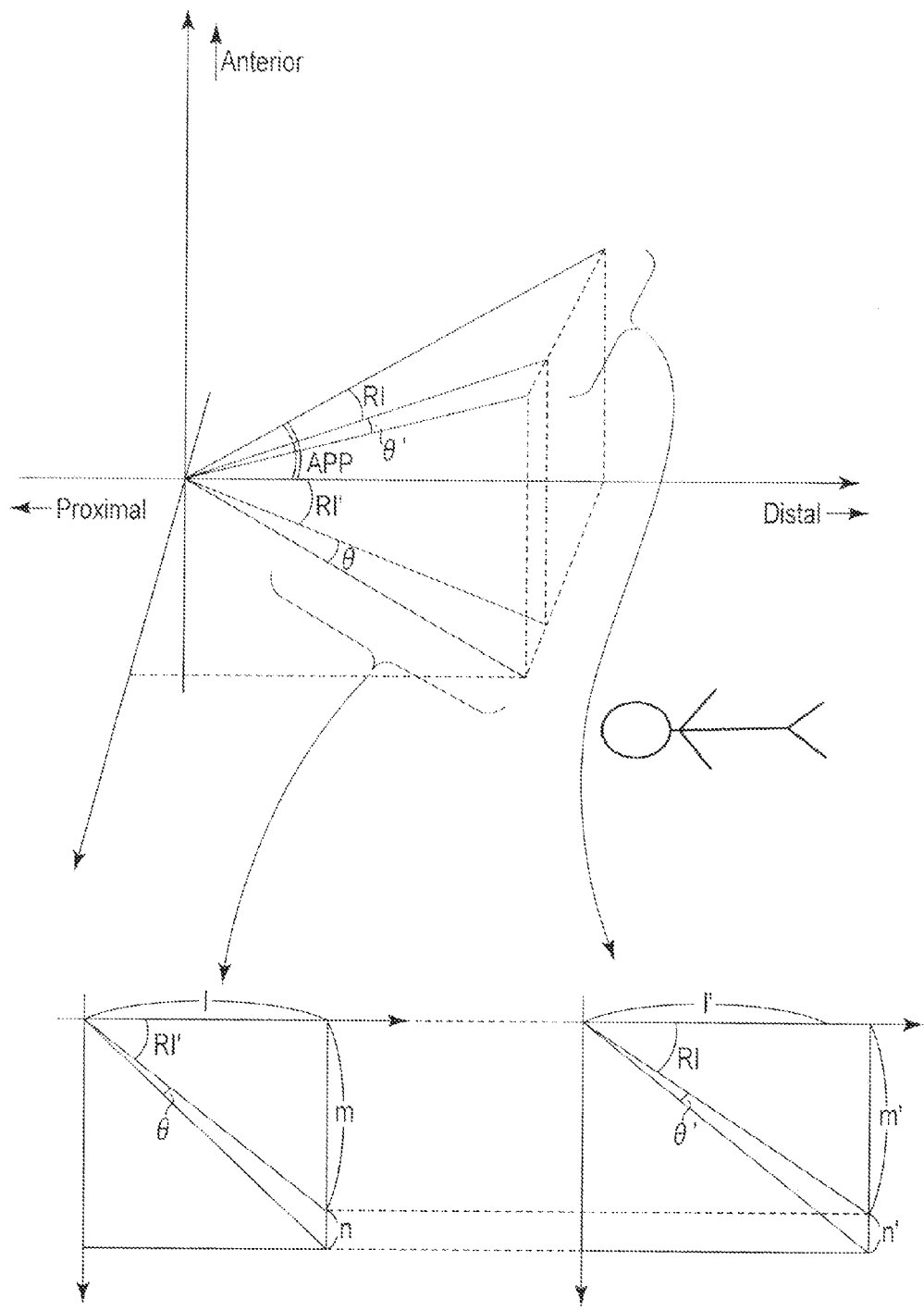
F I G. 36

PREOPERATIVE PLANNING PROGRAM AND OPERATION SUPPORT JIG FOR HIP REPLACEMENT ARTHROPLASTY

CROSS REFERENCE TO RELATED APPLICATIONS

This application is a Continuation Application of PCT Application No. PCT/JP2010/070931, filed Nov. 24, 2010 and based upon and claiming the benefit of priority from prior Japanese Patent Application No. 2009-266649, filed Nov. 24, 2009, the entire contents of which are incorporated herein by reference.

BACKGROUND OF THE INVENTION

1. Field of the Invention

The present invention relates to a preoperative planning program and an operation support jig for hip replacement arthroplasty using a data processing apparatus such as a personal computer.

2. Description of the Related Art

A knee joint or a hip joint constituting a part of human lower extremities is a particularly important joint for walking and others in daily life. Because of such a high requirement, such a joint is a region which is apt to suffer a traumatic injury, has a joint cartilage that is subjected to degenerative destruction with aging, and is often led to arthroplasty.

As a surgical treatment for this arthroplasty, total arthroplasty for removing a destroyed cartilage, implanting metal in this part, and surgically creating a joint function by contact of this metal and plastic such as polyethylene is currently provided all over the world as the most stable method that can improve the function.

At this time, future durability of a prosthetic joint is greatly affected by respective installation positions of a femoral component and a tibial component in a knee prosthesis and a femoral stem and an acetabular cup in a hip prosthesis, i.e., precision of extraction of each bone (osteotomy).

In conventional technologies, as to installation of this joint prosthesis, a contour of the joint prosthesis printed on a transparent sheet is superimposed on an X-ray image acquired from a front side and a lateral side before a surgical operation to determine positions or sizes of the components, the stem, and the cup. However, according to such a method, grasping of a bone shape is affected by an imaging direction of the X-ray image or a patient's position at the time of imaging, and precision is insufficient.

To solve this problem, there has been considered a method using computer software that performs X-ray imaging in two directions at an oblique angle of 60° with respect to a frontal view in a standing position by using a special imaging platform which is positioned between a film and an irradiation point in a calibration frame in advance, aligns a three-dimensional model of a bone shape created from an X-ray CT device or an MRI device to each bone shade with respect to this acquired image (image matching), and three-dimensionally grasps a bone shape in the standing posture as a reference of an installation position.

According to this method using the computer software, sizes and positions of the joint prostheses matched to the bone shapes and a load environment can be determined by reading out three-dimensional shape models using computer-aided design (CAD) data of the joint prostheses (see, e.g., Jpn. Pat. Appln. KOKAI Publication No. 2004-008707 (which will be referred to as "Patent Literature 1" hereinafter).

However, the technology described in Patent Literature 1 merely enables a surgeon to easily know a bone resection face on a tibial side in knee replacement arthroplasty, and it can not be applied to the femoral side having a different bone shape or function axis or any other joint, e.g., a hip joint, which is likewise important in the lower extremities, as it is.

Therefore, in regard to the hip replacement arthroplasty, there has been desired provision of a preoperative planning program and an operation support jig for hip replacement arthroplasty which enable appropriately reflecting individual differences of a patient to accurately determine a reaming procedure of a pelvic acetabulum before an operation and managing a surgical operation accurately reproducing preoperative determined contents during the operation.

BRIEF SUMMARY OF THE INVENTION

According to an aspect of the present invention, there is provided a preoperative planning program for hip replacement arthroplasty, the program characterized by causing a computer to execute: an image input step of inputting two-dimensional tomographic images of a patient's lower extremities including a pelvis and a femur; an image reconstruction step of reconstructing a three-dimensional image of the patient's lower extremities including the pelvis and the femur from the two-dimensional tomographic images input at the image input step; a joint prostheses determination step of determining installation positions and installation directions of joint prostheses which are installed in a pelvic acetabulum from the three-dimensional image of the pelvis and the femur obtained at the image reconstruction step; a base jig setting step of setting a three-dimensional image of a base jig having three or more columnar supports which abut on three or more reference points of the pelvis with respect to the three-dimensional image of the pelvis obtained at the image reconstruction step; and a parameter acquisition step of parameterizing and acquiring a direction of an indicator which runs through a predetermined position on the base jig in the three-dimensional image of the base jig set at the base jig setting step and becomes parallel to the installation direction of the joint prostheses determined at the joint prostheses determination step.

According to another aspect of the present invention, there is provided an operation support jig, characterized by comprising: a base jig including three or more columnar supports whose intervals are adjustable with respect to a frame body forming one plane; and a direction indicating jig which is disposed at a predetermined position on a surface of the frame body and includes an indicator which indicates an arbitrary direction and angle based on a plane of the frame body.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is a view showing a preoperative processing stage according to the embodiment;

FIG. 7 is a view showing a preoperative processing stage according to the embodiment;

FIG. 10B is an enlarged view showing a right portion of a screen in FIG. 10A;

FIG. 11 is a view showing a preoperative processing stage according to the embodiment;

FIG. 12 is a view showing a preoperative processing stage according to the embodiment;

FIG. 13B is an enlarged view showing a right portion of a screen in FIG. 13A;

FIG. 18 is a view showing a preoperative processing stage according to the embodiment;

FIG. 19 is a view showing a preoperative processing stage according to the embodiment;

FIG. 22 is a view showing a preoperative processing stage according to the embodiment;

FIG. 36 is a view showing the process of validating the accuracy of the base jig according to the embodiment.

DETAILED DESCRIPTION OF THE INVENTION

Embodiments according to the present invention will now be described hereinafter with reference to the accompanying drawings.

Figure 1:
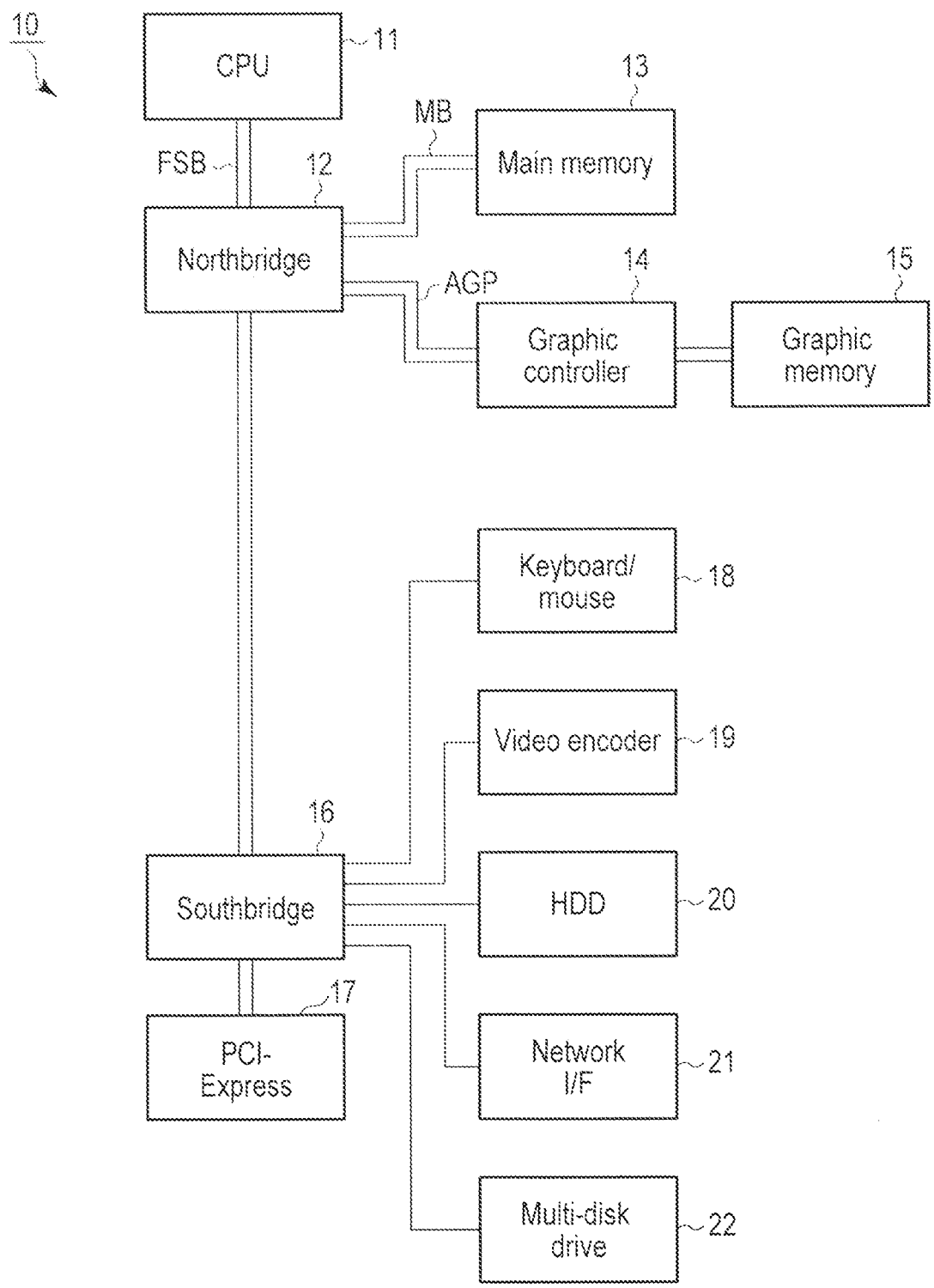
FIG. 1 is a block diagram showing a hardware configuration of a personal computer having a preoperative planning program for hip replacement arthroplasty installed therein according to an embodiment of the present invention.

FIG. 1 is a view showing a hardware configuration of a personal computer (which will be referred to as a "PC" hereinafter) 10 having a preoperative planning program for hip replacement arthroplasty installed therein. A CPU 11 that controls various kinds of processing is connected to a northbridge 12 through a front side bus FSB.

This northbridge 12 is connected to a main memory 13 through a memory bus MB, connected to a graphic controller 14 and a graphic memory 15 through a graphics interface AGP, and also connected to a southbridge 16 to execute input/output control between these members.

The southbridge 16 is connected to a PCI-Express bus 17, a keyboard/mouse 18, a video encoder 19, a hard disk drive (HDD) 20, a network interface (I/F) 21, and a multi-disk drive 22 to mainly execute input/output control between these peripheral circuits and the northbridge 12.

It is assumed that an operating system (OS), various kinds of application programs, various kinds of data files, a preoperative planning program for hip replacement arthroplasty, associated shape data of a joint prosthesis or later-described various jigs, and others are installed in the hard disk drive 20 in advance.

It is to be noted that the video encoder 19 generates and outputs an RGB video signal which is an image signal having an analog value from a supplied image signal having a digital value, and an image is displayed by supplying this signal to a display unit which is not shown in this example.

Further, the multi-disk drive 22 can perform reproduction and recording with respect to an optical disk medium based on, e.g., a compact disc (CD) standard or a digital versatile disc (DVD) standard, and it can input pieces of two-dimensional data of a patient's lower extremities and record them in the hard disk drive 20 by carrying out reproduction and reading with respect to the optical disk medium which has the patient's X-ray images, tomograms of an X-ray CT device or an MRI device, and others recorded therein.

It is to be noted that these individual elements constituting the PC 10 are nearly universal known technologies, and hence a description thereof will be omitted.

An operation of the embodiment will now be described.

Figure 2:
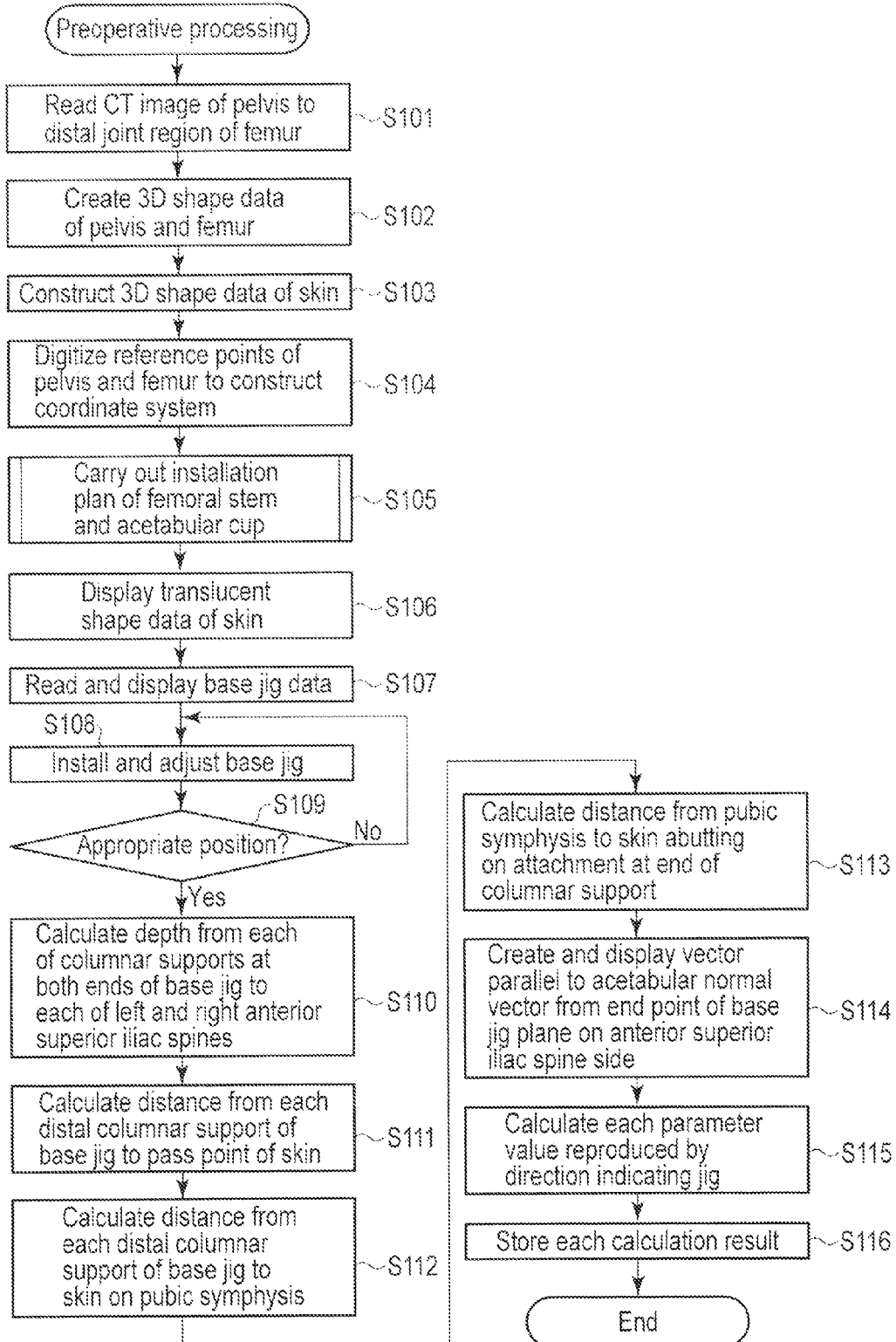
FIG. 2 is a flowchart showing processing contents of a main routine of a preoperative planning program according to the embodiment.
Figure 3:
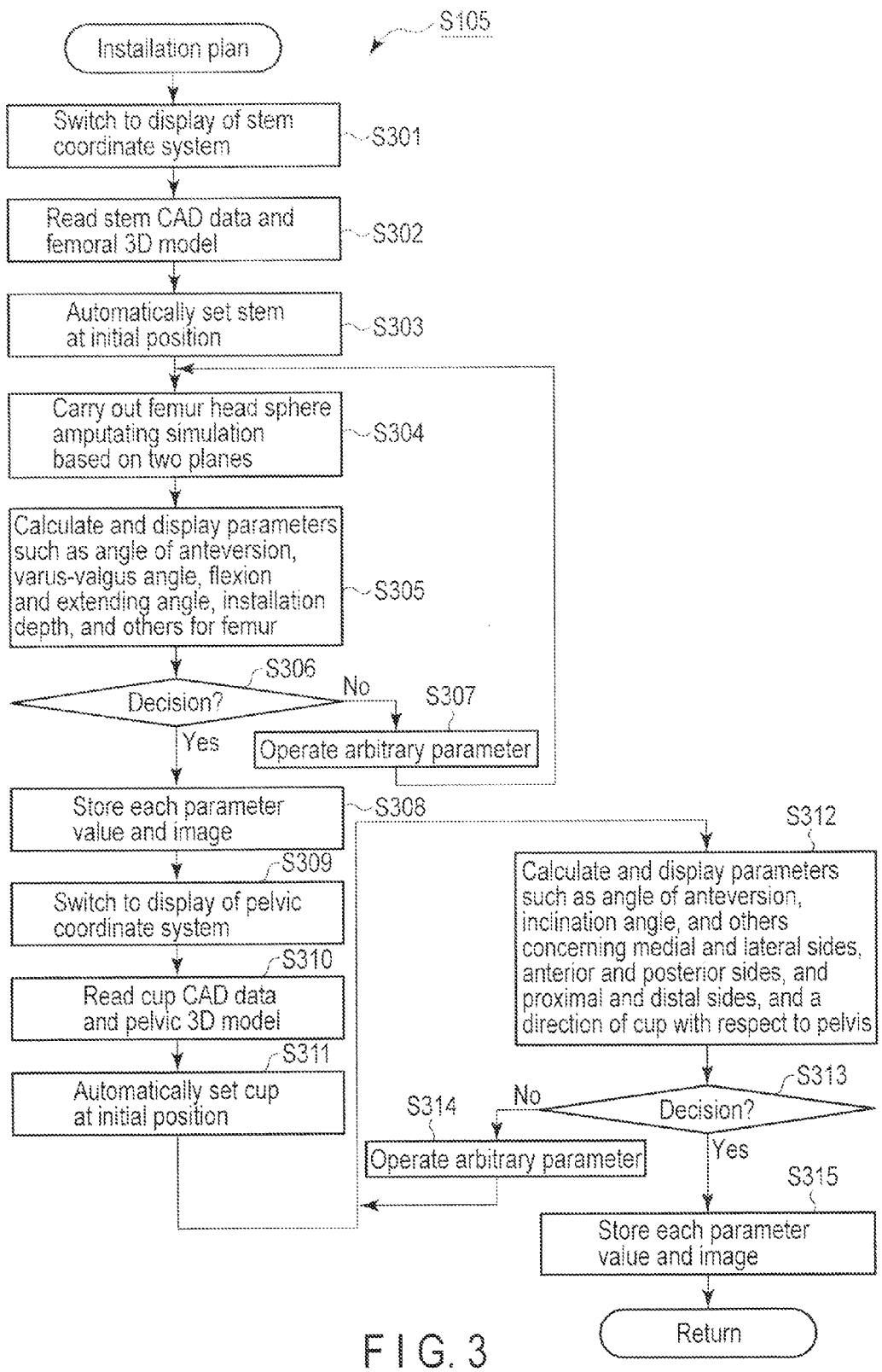
FIG. 3 is a flowchart showing processing contents of a sub-routine of an installation plan for a femoral stem and an acetabular cup in FIG. 2 according to the embodiment.

FIG. 2 and FIG. 3 show processing contents of this embodiment that the preoperative planning program stored in the hard disk drive 20 is initiated by a surgeon who is a user of this PC 10 and executed by the CPU 11.

In FIG. 2 and FIG. 3, processing required to acquire various parameters which are necessary for installation of a femoral-side joint prosthesis (which will be also referred to as a "femoral stem" hereinafter) is partially simplified, and processing required to acquire various parameters which are necessary for installation of a pelvic-side joint prosthesis will be mainly explained.

In case of executing this preoperative planning program, it is assumed that two-dimensional image data of a patient's lower extremities which is a two-dimensional tomographic image data slice acquired by the X-ray CT device or the MRI device is read and stored in the hard disk drive 20.

Furthermore, three-dimensional data of the joint prosthesis and various jigs used during the operation is additionally prepared and stored in the hard disk drive 20 in advance.

Therefore, when the preoperative planning program shown in FIG. 2 and FIG. 3 is initiated, a graphical user interface (GUI) is displayed in a screen of the display unit connected to the video encoder 19, and a folder storing two-dimensional image data of lower extremities obtained by shooting a region including at least left and right anterior superior iliac spines and femurs from a distal position to a proximal position of a desired displayed patient is selected in this GUI.

The selected two-dimensional image data of the lower extremities is read out from the folder in the hard disk drive 20 (step S101), three-dimensional data of a pelvis and the femurs is created, and this image is displayed in the display screen (step S102).

Figure 4:
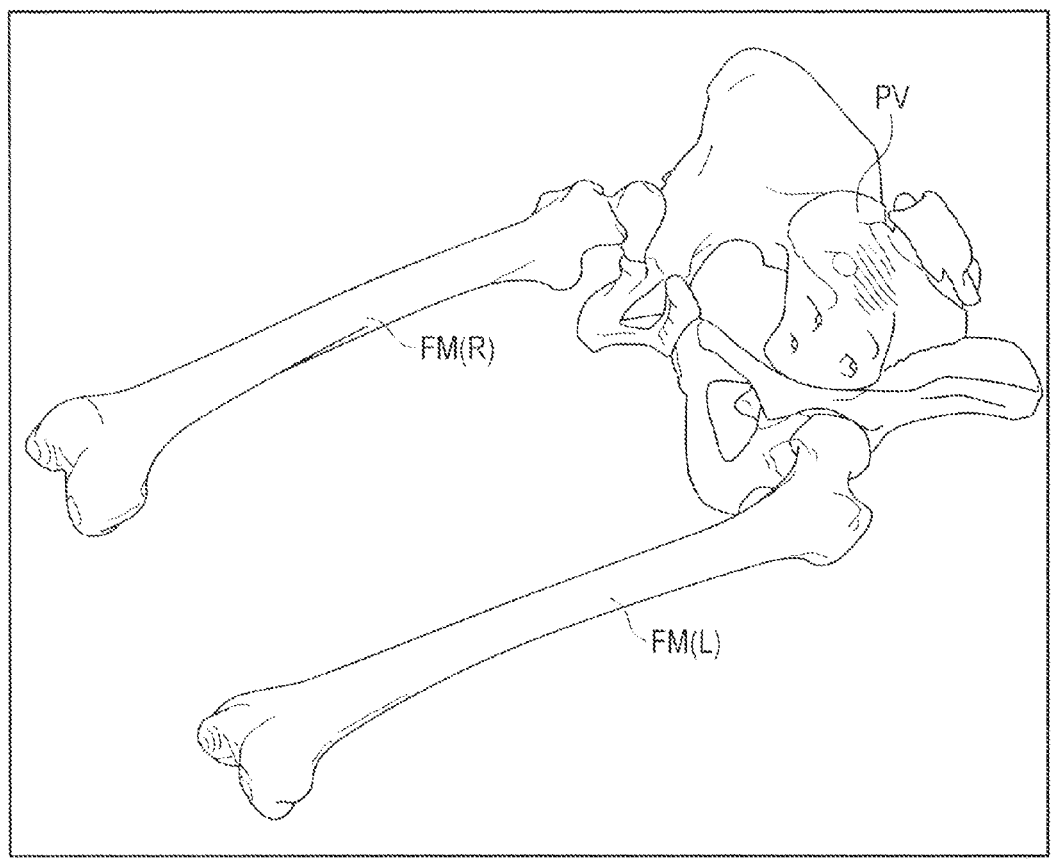
FIG. 4 is a view showing a preoperative processing stage according to the embodiment.

FIG. 4 shows an example of a three-dimensional shape image of the pelvis PV and the left and right femurs FM(L) and FM(R) displayed in the display screen at this moment.

The three-dimensional data may be polygonal or curved surface shape data, or three-dimensional volume display using volume rendering may be carried out in place of creating shape data.

Figure 5:
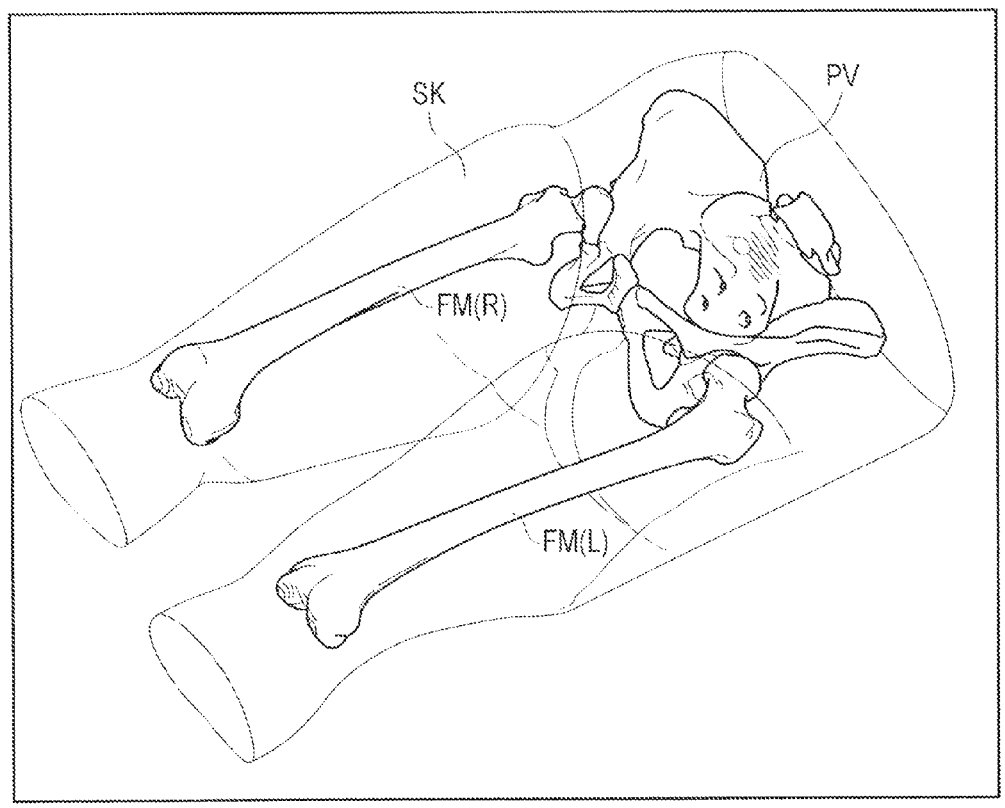
FIG. 5 is a view showing a preoperative processing stage according to the embodiment.

Subsequently, such a three-dimensional shape data of skin as shown in FIG. 5 is constructed (step S103). This drawing shows an example that translucent skin SK is displayed with respect to the pelvis PV and the left and right femurs FM(L) and EM(R). The construction of this three-dimensional data of the skin is not necessary, and three-dimensional volume display using volume rendering may substitute for this construction. The display of the skin used to three-dimensionally grasp a positional relationship between the pelvis and the femurs in a body in a recumbent position.

Alternatively, a three-dimensional model of the skin is not necessarily required if distances from a surface of the skin to the left and right anterior superior iliac spines and a pubic symphysis as bone landmarks (reference points) can be measured or the distances from the surface of the skin to the left and right anterior superior iliac spines and the pubic symphysis can be statistically grasped by directly observing a CT tomographic image.

Then, the reference points (the landmarks) of the pelvis and the femurs are digitized by using operations of the keyboard/mouse 18 to construct a coordinate system (step S104).

FIG. 6 shows reference points for the pelvis and the femur are indicated by black rectangles. On the pelvis PV side, the left and right anterior superior iliac spines LM11 and LM12 and the pubic symphysis LM13 are determined as the reference points, and the coordinate system is constructed based on these reference points.

On the femur FM side, a center LM 21 and a circle LM 22 of a femur head sphere on the hip joint side and medial and lateral condyles LM23 and LM24 on the knee joint side are determined as the reference points, and the coordinate system is constructed based on these points.

Although FIG. 6 shows the reference points of the left femur FM alone, the reference points of the right femur FM are also similarly digitized.

The reference points are also used for the purposes other than the construction of the coordinate system. Specifically, a greater trochanter point and posterior points of medial and lateral condyles are digitized.

The coordinate system is set for the convenience's sake, and a coordinate system using other reference points may be used.

FIG. 7 shows a coordinate system of the pelvis PV. The coordinate system is constructed based on a plane formed of a triangle obtained by connecting three points, i.e., the left and right anterior superior iliac spines LM11 and LM12 and the pubic symphysis LM13 (which will be referred to as an "APP plane" hereinafter). Specifically, the pubic symphysis LM13 is determined as an origin, and a line parallel to a line connecting the left and right anterior superior iliac spines LM11 and LM12 with each other is determined as an X-axis. As a matter of convenience, a right side of the body is determined as a + (positive) side. Moreover, an axis orthogonal to the X-axis along the APP plane is determined as a Z-axis, and an axis orthogonal to the APP plane is determined as a Y-axis. It is to be noted that a description on the construction of the coordinate system of the femur side will be omitted.

After the coordinate system is constructed as described above, a plan for installing a femoral stem and an acetabular cup is created using a CT image or a multiple planner reconstruction (MPR) image based on the CT image (step S105).

FIG. 3 is a sub-routine showing detailed processing contents of the installation plan of step S105. At the beginning, the screen is changed to display of a stem coordinate system (step S301). CAD data of the femoral stem is read out from the HDD 20 (step S302), and a three-dimensional model of the femur FM as an installation target is displayed together with a model of the stem.

Figure 8:
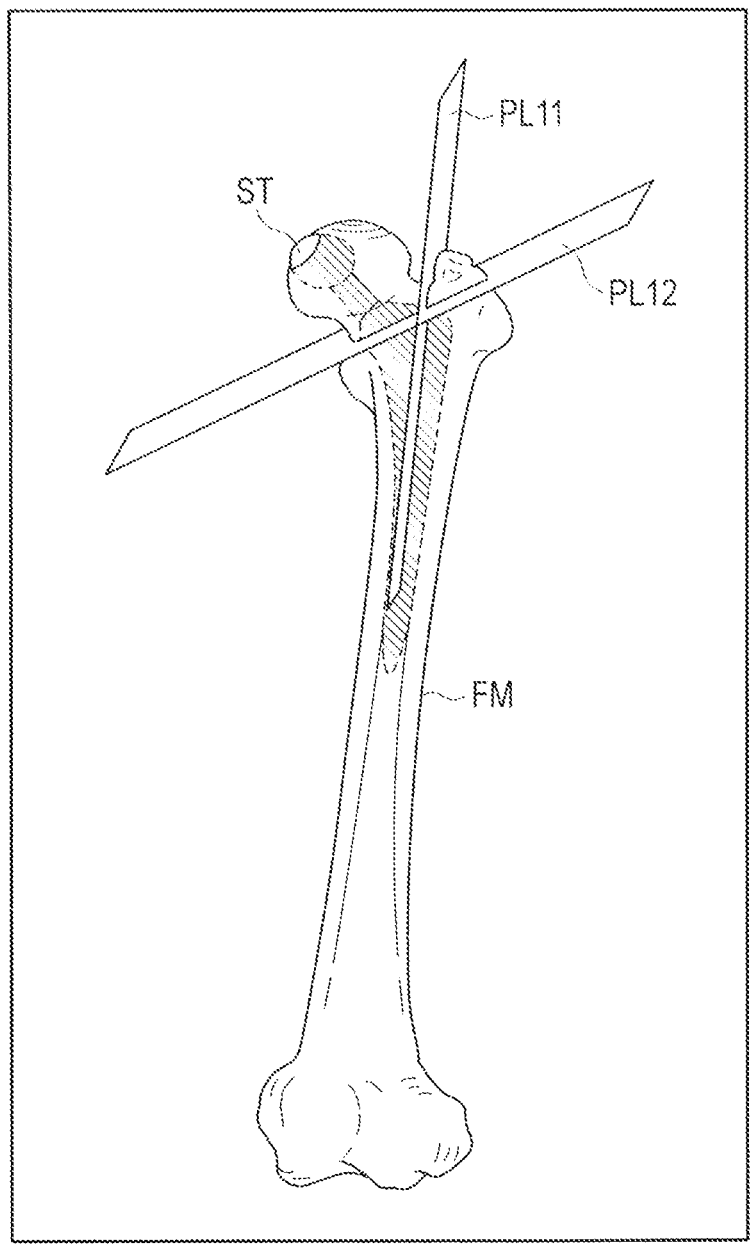
FIG. 8 is a view showing a preoperative processing stage according to the embodiment.

FIG. 8 shows a state that the femur FM and the femoral stem ST are displayed in the display screen. As shown in the drawing, the femoral stem ST is automatically installed at a determined initial position (step S303). In this case, the initial position is determined from the reference points and shape data on the femur FM side as the installation target and the reference points set on the femoral stem ST based on, e.g., an installation position recommended by the academic society and also recommended by a manufacturer of the femoral stem ST.

For example, an axis of the femoral stem ST can be conformed to a proximal bone axis of the femur FM, a bone head center of the femoral stem ST can be conformed to a height of the greater trochanter point of the femur FM, and a position anteverted 40° from a line connecting the medial and lateral anterior condyle rearmost points of the femur FM in a rotating direction can be determined as an initial position.

Additionally, in an installation position simulation of the femoral stem ST, simulation of amputating the femur head sphere portion in the three-dimensional shape model of the femur FM at the same position as that in a surgical treatment is performed (step S304).

This amputating simulation is performed by combining two planes shown in FIG. 8. An initial position of a first plane PL11 is displayed at a position which is parallel to a YZ plane of the femoral stem ST and runs through a stem axis. Although a second plane is a plane substantially orthogonal to a neck axis of the femoral stem ST, an appropriate direction of this plane is previously defined in accordance with a type of the femoral stem ST.

These two planes PL 11 and PL 12 can be arbitrarily translated and rotated in accordance with an operation using the keyboard/mouse 18.

The amputating operation can be carried out by using these two planes to resect the femur head sphere side.

In regard to the femoral stem ST automatically installed at the determined initial position, parameters such as an angle of anteversion, a varus-valgus angle, a flexion and extending angle, an installation depth, and others with respect to the femur FM are calculated and displayed in the screen (step S305).

The medial and lateral sides, the anterior and posterior sides, the proximal and distal sides, flexion and extension, value and valgus, and anteversion and retrotorsion are freely moved and changed by operating the keyboard/mouse 18 in regard to a position and a direction of the thus displayed installation state based on the coordinate system of the femur stem ST, whereby the surgeon who is a user can effect the installation at an appropriate position.

That is, when there is any operation of the keyboard/mouse 18, a judgment is made upon whether this operation determines a position that is set at this moment is a final installation position (step S306).

When it is determined that the operation does not instruct to make a final decision and an arbitrary parameter associated with the operation is thereby changed to vary the installation position (step S307), the control returns to the processing starting from step S304 in accordance with this change to execute adjustment of the two planes for performing the osteotomy and subsequent readjustment of each parameter.

In this manner, the processing of steps S304 to S307 is repeatedly carried out. Further, when the user operates the keyboard/mouse 18 to decide the installation position at the moment of determining that the femoral stem ST was successfully moved to the installation position which is considered to be optimum, this decision is determined in step S306, each parameter value at that time is stored as three-dimensional positional information of a cut surface shape of the femur, and image data is also stored as required (step S308).

Figure 9:
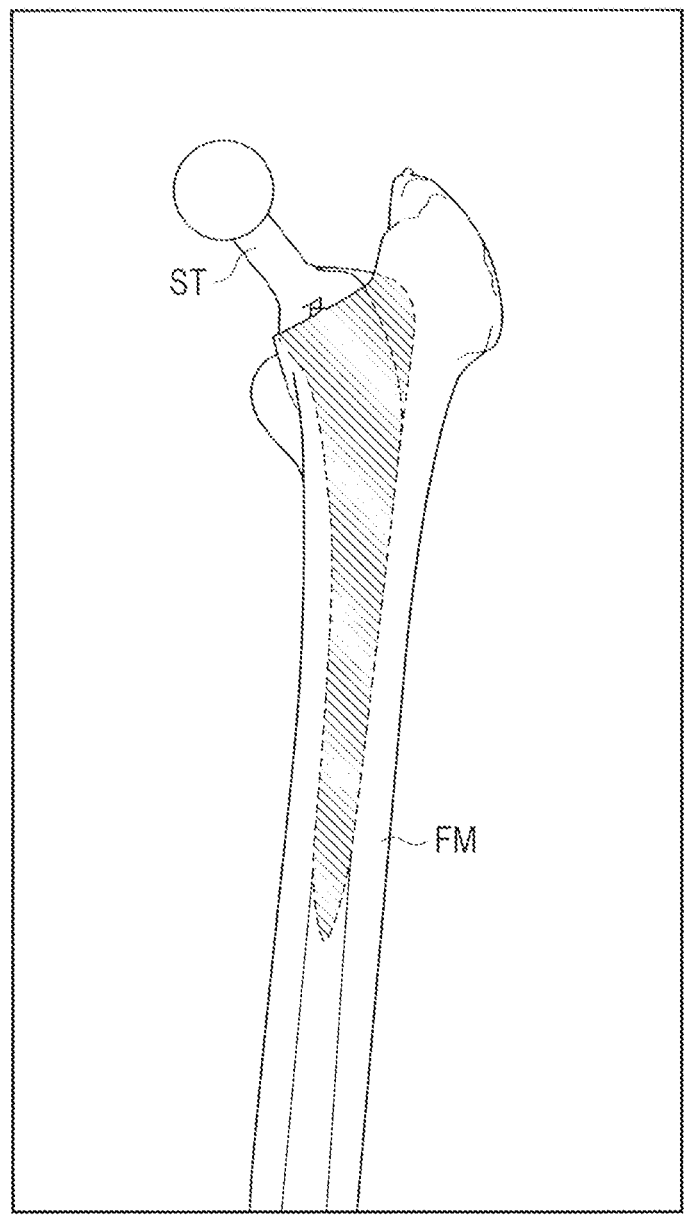
FIG. 9 is a view showing a preoperative processing stage according to the embodiment.

FIG. 9 shows an example of an image when the bone head of the femur FM is cut off and the femoral stem ST is installed. When such an image has been stored, reference can be made to a position and a cut surface shape in amputation of a femoral head during a surgical treatment. Furthermore, when an angle of anteversion of the femoral stem ST with respect to the cross-sectional shape is observed, the accurate angle of anteversion of the femoral stem ST can be realized.

The processing on the femur FM side is finished, and the processing on the pelvis PV side will now begins.

First, the screen is changed to display of the pelvic coordinate system (step S309). CAD data of the acetabular cup and a three-dimensional model of the pelvis are read out from the HDD 20 (step S310), both these pieces of data are displayed in the display.

Figure 10A:
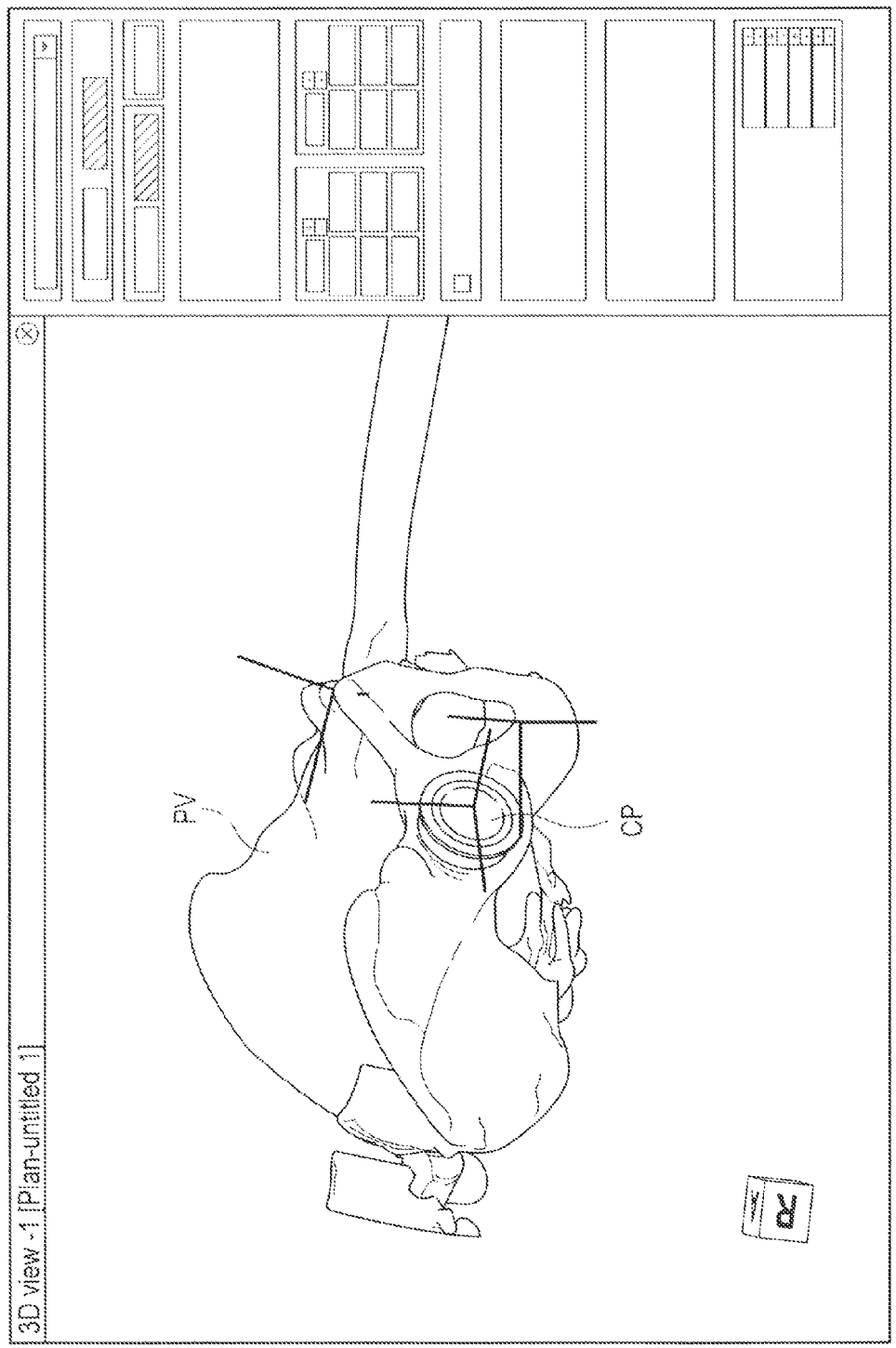
FIG. 10A is a view showing a preoperative processing stage according to the embodiment.

FIG. 10A shows an example of a state that the pelvis PV and the acetabular cup CP are shown in the display screen. FIG. 10B shows a right portion of the screen in FIG. 10A in an enlarging manner. As shown in these drawings, the acetabular cup CP is automatically installed at a determined initial position (step S311). The initial position in this case is determined from the reference points and shape data on the femur FM side as the installation target and the reference points set on the femoral stem ST based on, e.g., an installation position recommended by the academic society and also recommended by a manufacturer of the femoral stem ST.

For example, the innermost point of an acetabulum of the pelvis PV can be digitized as a reference point, and an angle of anteversion of 20° and an inclination angle of 40° in a pelvic coordinate system can be determined as initial positions.

In regard to the acetabular cup CP automatically installed in the determined initial position, medial and lateral sides, anterior and posterior sides, proximal and distal sides, an angle of anteversion and an inclination angle concerning a direction, and others with respect to the pelvis PV are calculated and displayed in the screen (step S312).

The medial and lateral sides, the anterior and posterior sides, the proximal and distal sides, and the angle of anteversion and the inclination angle concerning a direction are freely moved and changed with respect to the thus displayed installation state by operating the keyboard/mouse 18 in regard to a position and a direction of the acetabular cup CP based on the pelvic coordinate system, whereby the surgeon who is a user can effect the installation at an appropriate position.

That is, when there is any operation of the keyboard/mouse 18, a judgment is made upon whether this operation determines a position that is set at this moment as a final installation position (step S313).

When it is determined that the operation does not instruct to make a final decision and an arbitrary parameter associated with the operation is thereby changed to vary the installation position (step S314), the control returns to the processing starting from step S312 in accordance with this change to execute adjustment of a position and a direction for performing reaming and subsequent readjustment of each parameter.

At the time of this adjustment operation, the surgeon who is a user can arbitrarily and freely switch not only the pelvic coordinate system but also a femoral coordinate system, a stem coordinate system, a cup coordinate system, and a CT coordinate system as a coordinate system to be used.

Additionally, the joint prosthesis can be installed while confirming a reduced leg position. FIG. 11 shows an example of a joint prosthesis installation state in a non-reduced leg position mode, and FIG. 12 shows an example of a joint prosthesis installation state in a reduced leg position mode. When the reduced leg position mode is selected, the femur FM and the femoral stem ST move together in such a manner that central positions of the acetabular cup CP and the femoral stem ST coincide with each other, a leg length reduction amount, three-dimensional distances between the anterior superior iliac spine and the greater trochanter, and others are changed and displayed in accordance with this movement.

In this manner, the processing of steps S312 to S314 is repeatedly executed. Further, when the user operates the keyboard/mouse 18 to decide the installation position at the moment of determining that the acetabular cup CP was successfully moved to the installation position which is considered to be optimum, this decision is determined in step S313, each parameter value at that time is stored as three-dimensional positional and directional information of reaming of the pelvis, and image data is also stored as required (step S315).

Figure 13A:
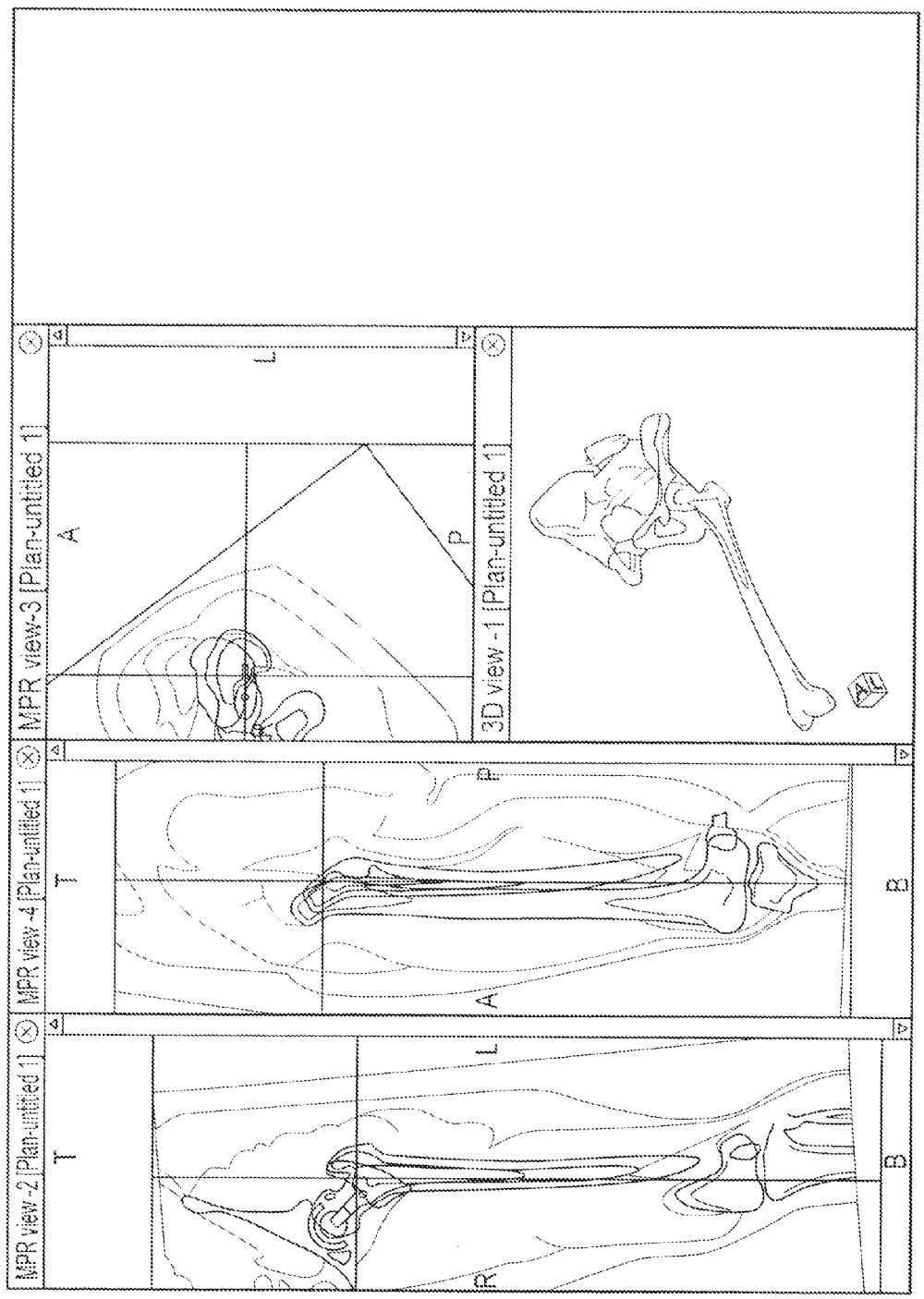
FIG. 13A is a view showing a preoperative processing stage according to the embodiment.

FIG. 13A shows an example of displaying installation states of the femoral stem ST and the acetabular cup CP in the stem (left) coordinate system. FIG. 13B shows a right portion of the screen in FIG. 13A in an enlarging manner.

The processing of the joint prosthesis installation plan is finished, and the sub-routine in FIG. 3 is ended, and the control returns to the main routine in FIG. 2.

In FIG. 2, a three-dimensional image of the pelvis PV and the femur FM is displayed in a supine position, and the translucent image of the skin shape data is also displayed (step S106).

Figure 14:
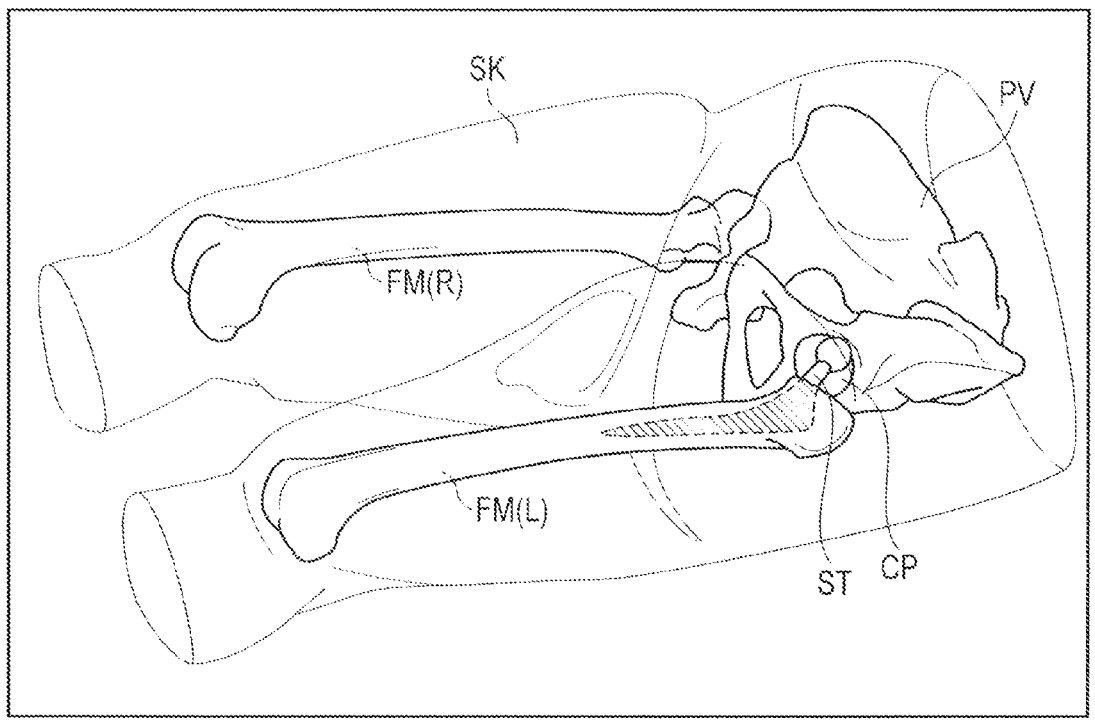
FIG. 14 is a view showing a preoperative processing stage according to the embodiment.

FIG. 14 shows an example that a translucent image of the skin SK is displayed with respect to the pelvis PV, the left and right femurs FM, the acetabular cup CP, and the femoral stem ST.

Then, CAD data of the base jig is read out from the HDD 20, and an image showing that the base jig is installed on a body surface is displayed based on the read data of the base jig by using as a guide a position facing a plane constituted of the left and right anterior superior iliac spines and the pubic symphysis (an APP plane) in the supine position (step S107).

Figure 15:
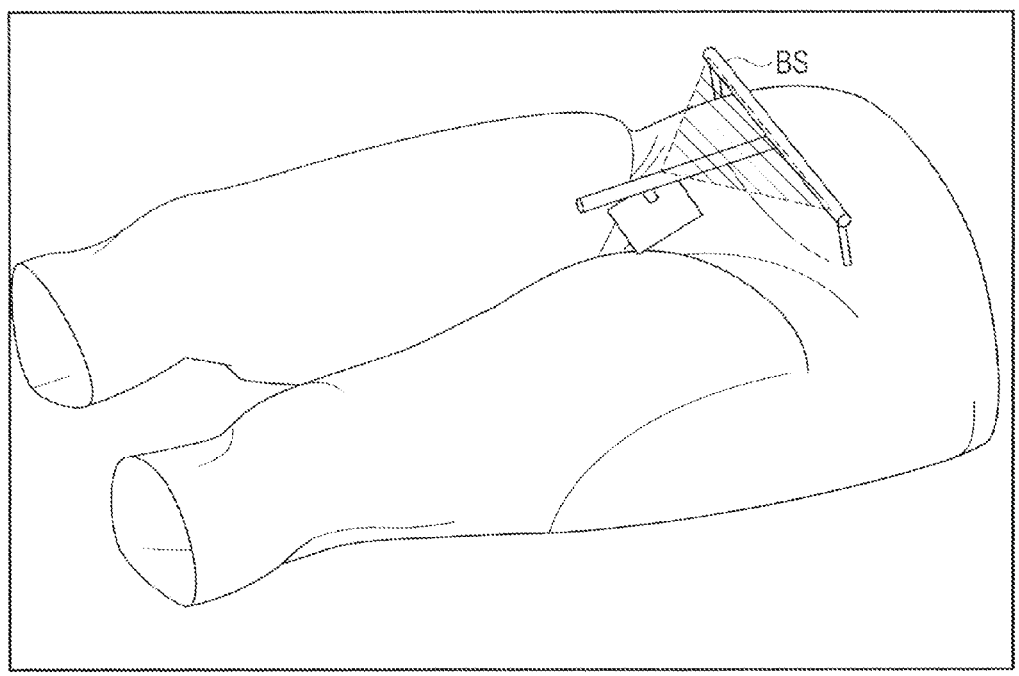
FIG. 15 is a view showing a preoperative processing stage according to the embodiment.
Figure 16:
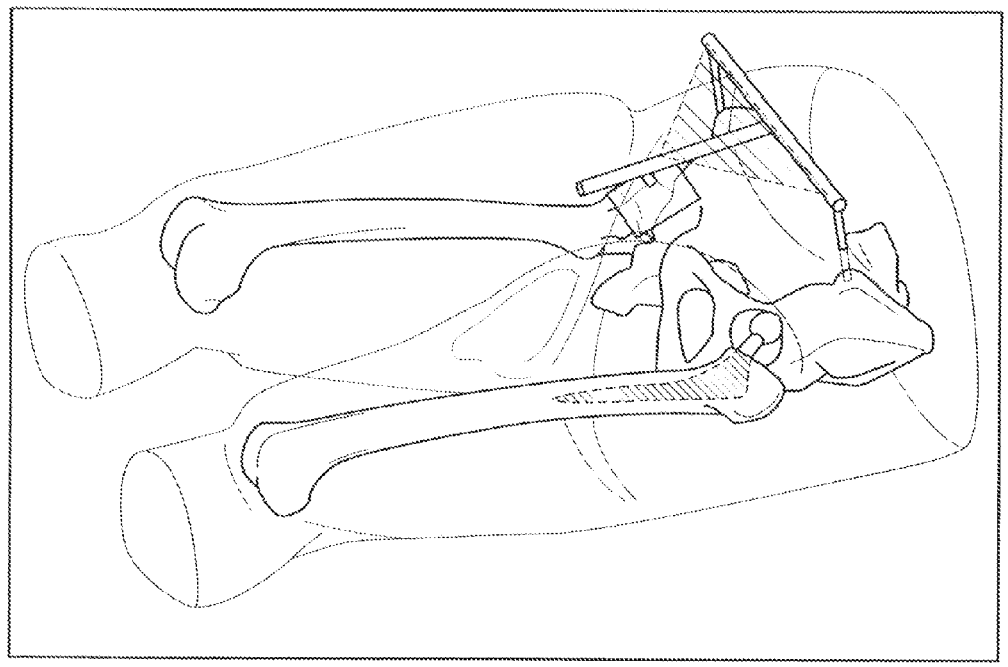
FIG. 16 is a view showing a preoperative processing stage according to the embodiment.

Each of FIG. 15 and FIG. 16 shows an example of an image that the base jig BS is installed at a corresponding position. The base jig BS has a shape based on an inverted triangle, and it has columnar supports, which are substantially vertical to the above-described plane, at lower portions of three point positions. A distance between two points corresponding to an upper side of the inverted triangle can be adjusted in accordance with a gap between the left and right anterior superior iliac spines.

Further, an end of each columnar support coming into contact with the left and right anterior superior iliac spines is formed as a sharp pin so that the pin can be stuck into and fixed in the anterior superior iliac spines from the skin portion of the left and right anterior superior iliac spines, or a sharp pin portion may be attachable with respect to an end of each columnar support so that the base jig BS alone can be removed in a state that the pin portion is stuck into and fixed in the left and right anterior superior iliac spines.

Furthermore, an end of the columnar support at a third point on a distal side serving as another vertex of the base jig BS is brought into contact with the body surface on the pubic symphysis. It is also possible to adjust a distance to the third point coming into contact with this pubic symphysis side with respect to the straight line connecting the two points on the side coming into contact with the left and right anterior superior iliac spines.

That is, as a specific configuration of the base jig BS, for example, two rail members are assembled into a T-like shape in such a manner that one of the members becomes orthogonal to the center of the other, and slider members each having a columnar support provided thereon is configured to be movable and fixable along the rail-like members, thereby adjusting a gap between the three positions.

Figure 17:
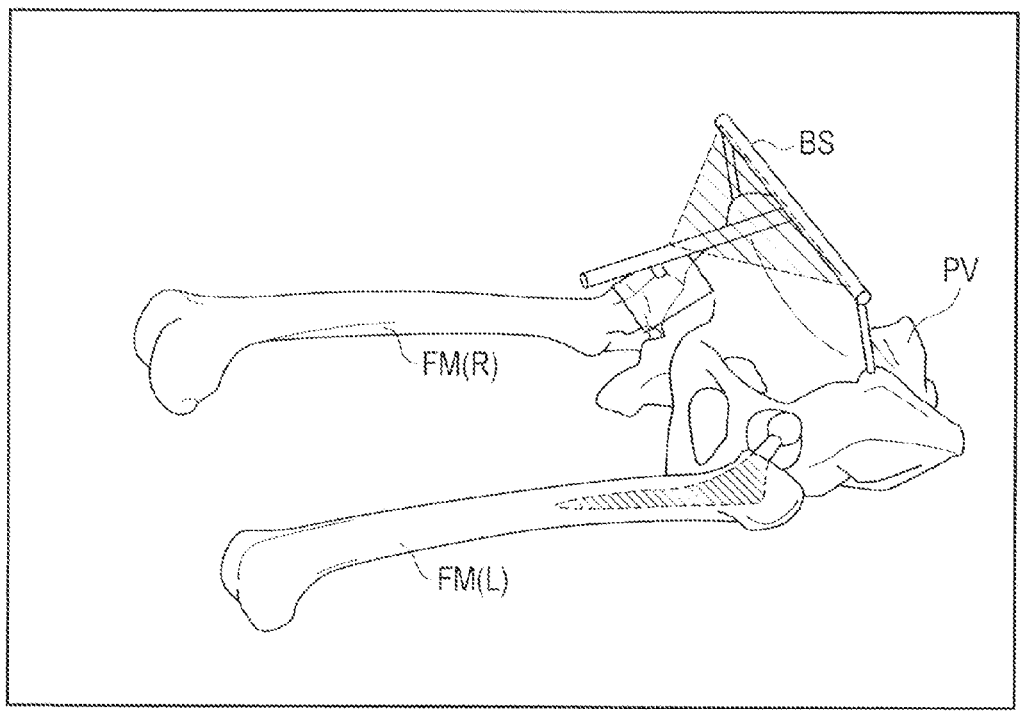
FIG. 17 is a view showing a preoperative processing stage according to the embodiment.

FIG. 17 shows a state of the base jig BS installed on the pelvis PV without the display of the skin SK being eliminated from FIG. 16.

The two columnar supports portions are fixed on the left and right anterior superior iliac spines of the patient by using the pin portions provided at the ends thereof, whereas the end of the columnar support portion on the pubic symphysis side is not fixed, but a plate having an appropriate size is disposed as shown in, FIGS. 15 to 17 so that the jig can be installed while widely coming into contact with the skin on the pubic symphysis.

Moreover, the end of the columnar support portion on the pubic symphysis side may be configured in such a manner that various attachments can be replaced, and an appropriate attachment may be selected and attached in accordance with a body type of a patient.

Additionally, to stabilize the base jig BS, the attachment coming into contact with the pubic symphysis may be attached to a cloth that covers the skin on the pubic symphysis by using an adhesive tape.

In a state that the end of each columnar support portion of the base jig BS is in contact with the left and right anterior superior iliac spines and the pubic symphysis as shown in FIG. 15 to FIG. 17, a distance in a depth direction from the columnar support portion of the base jig BS on the left and right anterior superior iliac spines to the left and right anterior superior iliac spines is calculated and displayed in the display (step S110).

Further, a distance from an attachment position of each columnar support of the base jig including a leg Length to a pass point of the skin is also calculated and displayed (step S111).

As a result, when scale marks are engraved or printed on each columnar support portion of the base jig and they are read, these marks can be used as a guide indicating accuracy of pin fixation during a surgical treatment.

Likewise, on the line connecting the end of the columnar support portion on the distal side of the base jig with the pubic symphysis, a distance from the end of the columnar support portion to the surface of the skin is calculated, and it is displayed in the display (step S112).

Further, on the line connecting the end of the columnar support portion on the distal side with the pubic symphysis, a distance from the pubic symphysis to the surface of the skin coming into contact with the attachment disposed to the end of the columnar support portion is calculated, and it is displayed in the display (step S113).

Each of FIG. 18 (A) and FIG. 18 (B) shows an example that a distance from each of the left and right anterior superior iliac spines to the body surface is calculated and displayed in the display screen.

Furthermore, FIG. 19 (A) shows an example that a distance from the pubic symphysis to the skin surface is calculated and displayed in the display screen, and FIG. 19 (B) shows an example that a distance from the anterior superior iliac spine to the skins surface is calculated and displayed in the same.

Based on the above-described processing, a plane of the base jig BS with respect to the APP plane is determined, and a relationship between a normal vector of this plane and an acetabular normal vector is determined.

Therefore, to determine an acetabular reaming direction, a vector that is parallel to the acetabular normal vector is created from an end point of the plane of the base jig BS on the anterior superior iliac spine side, and the created vector is displayed as a direction indicating a later-described direction indicating jig (step S114).

Figure 20:
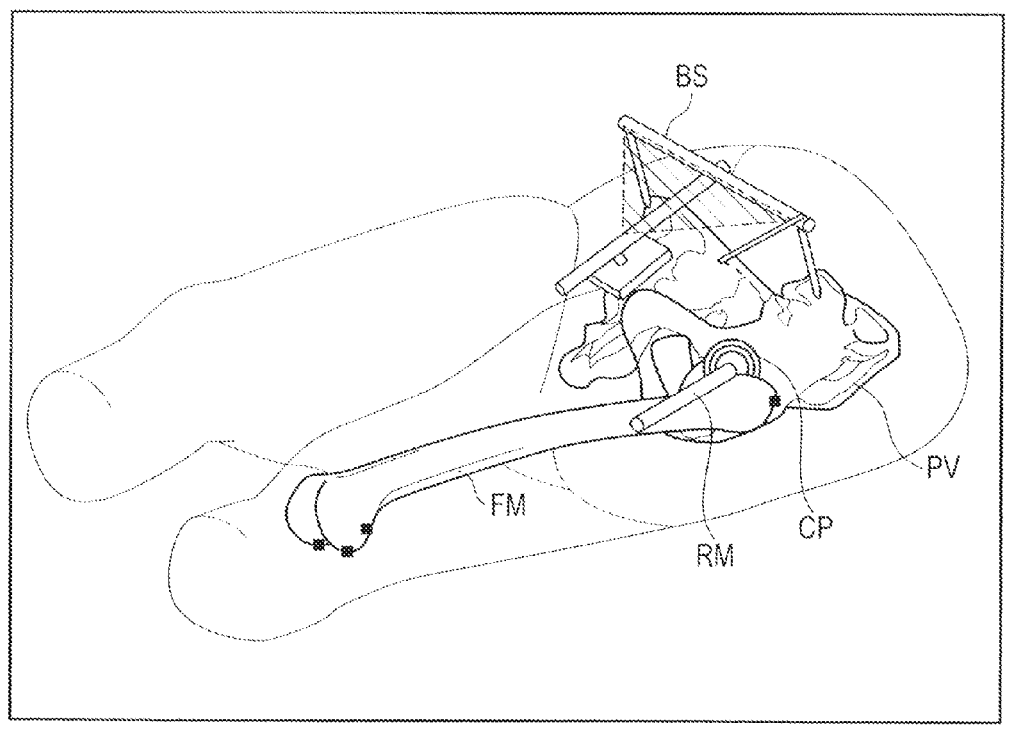
FIG. 20 is a view showing a preoperative processing stage according to the embodiment.

FIG. 20 shows an example that an acetabular reaming jig RM is disposed to the acetabulum of the pelvis PV and a fundamental direction indicating jig DI is disposed to the base jig BS. As a matter of course, the direction indicating jig DI is installed in such a manner that its axial direction becomes parallel to an axial direction of the acetabular reaming jig RM in accordance with installation of the acetabular reaming jig RM along the acetabular normal vector.

It is to be noted that, although an example of a specific configuration of the direction indicating jig DI that is actually used for a surgical treatment will be described later, the direction indicating jig DI may have a physical indicating rod or may be formed of an optical member that uses a laser pointer to visually indicate a direction.

Subsequently, to accurately reproduce a direction of the acetabular normal vector which is an installation direction of the acetabular cup CP during the surgical treatment, parameter values using the direction indicating jig DI are calculated (step S115).

Figure 21:
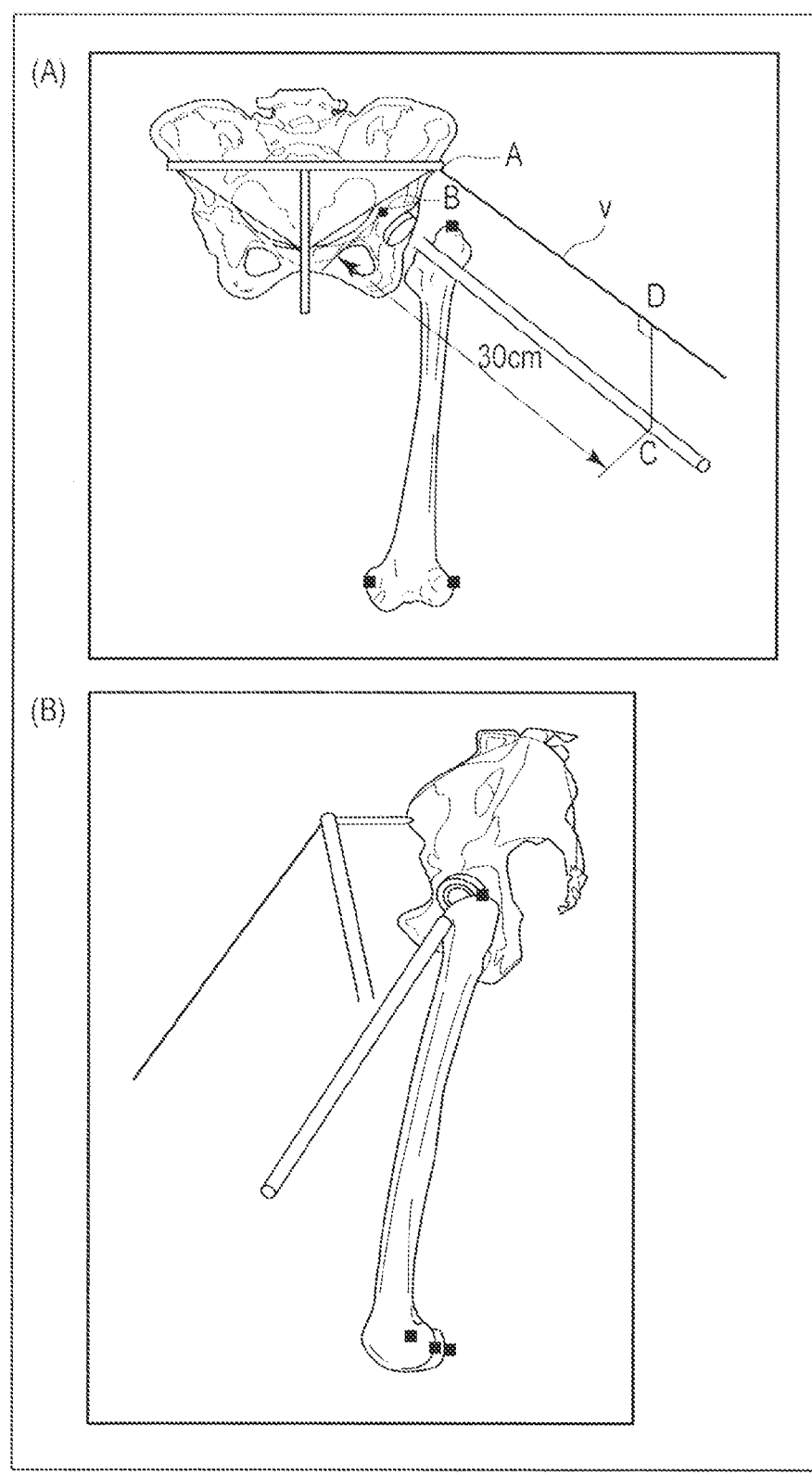
FIG. 21 is a view showing a preoperative processing stage according to the embodiment.

FIG. 21 (A), FIG. 21 (B), FIG. 22 (A), and FIG. 22 (B) are views for specifically explaining a process of calculating the parameter values. In these drawings, a vector v parallel to the acetabular normal vector is created from an end point of the base jig BS corresponding to the anterior superior iliac spine A. A point C on the acetabular normal vector that is apart from a cup vertex B by a fixed distance, e.g., 30 [cm] is defined, and an intersection D with respect to a perpendicular line extending downwards to the vector V from the point C is calculated. Moreover, angles formed between the acetabular normal vector and the plane of the base jig BS are defined as a coronary plane angle α and a sagittal plane angle β, and a distance AD, a distance CD, the angle α, and the angle β are calculated as the parameters.

As a result, the direction of the acetabular normal vector which is the installation direction of the acetabular cup CP can be uniquely obtained based on the base jig BS, and the installation parameters for the direction indicating jig DI associated with the acetabular normal vector can be acquired.

The thus obtained respective parameter values are stored in the HDD 20, and hence the preoperative processing in FIG. 2 is finished.

During the surgical treatment, the direction indicating jig DI configured to realize the direction of this acetabular normal vector is prepared, and the two angle parameters measured in the preoperative simulation, i.e., the angle α formed with the Z-axis of the base jig BS and the angle β formed between the vector v of the direction indicating jig DI and a line obtained by projecting the vector v onto the plane of the base jig BS are set to the direction indicating jig DI, thereby accurately setting the direction of the direction indicating jig DI in parallel to the acetabular normal vector.

Figure 23:
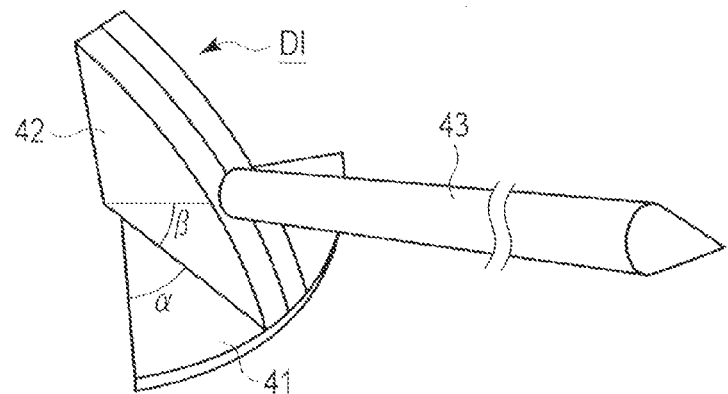
FIG. 23 is a view showing an appearance of a direction indicating jig according to the embodiment.

FIG. 23 shows an example of a configuration of the direction indicating jig DI. In the direction indicating jig DI depicted in the drawing, a β angle setter 42 having a fan-like shape is erected along a radial direction of an α angle setter 41 likewise having a fan-like shape. A direction indicating rod 43 whose radial direction can be arbitrarily changed is extended in a radial pattern from a peripheral side surface of the β angle setter 42 having the fan-like shape, and the direction of the vector v parallel to the acetabular normal vector can be reproduced by disposing the α angle setter 41 of the direction indicating jig DI to the base jig BS and then reproducing the angle α of the β angle setter 42 with respect to the α angle setter 41 and the angle β of the direction indicating rod 43 with respect to the β angle setter 42.

Figure 24:
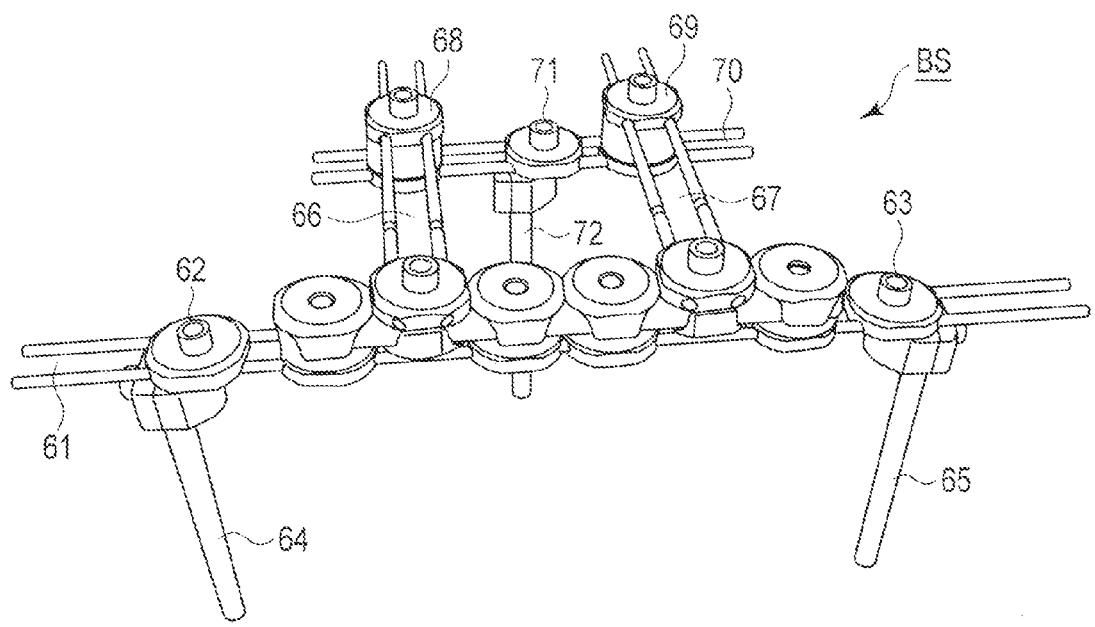
FIG. 24 is a view showing an appearance configuration of a base jig according to the embodiment.

FIG. 24 shows an example of a specific configuration of the base jig BS. In this drawing, movable and fixable slider members 62 and 63 are arranged on both end sides of a rail member 61 constituted of two metal rods, and columnar support portions 64 and 65 configured to abut on the left and right anterior superior iliac spines are disposed to lower portions of these slider members 62 and 63. The columnar support portion 64 on the slider member 62 side abuts on the anterior superior iliac spin on the patient's left side and, on the other hand, the columnar support portion 65 on the slider member 63 side abuts on the anterior superior iliac spine of the patient's right side.

Additionally, rail members 66 and 67 each of which is constituted of two metal rods are disposed from substantially central parts of the rail member 61 to be orthogonal to the rail member 61. Movable and fixable sliders 68 and 69 are disposed to these rail members 66 and 67, respectively. Further, a rail member 70 constituted of two metal rods is disposed to connect these sliders 68 and 69. Furthermore, a movable and fixable slider 71 is placed in a portion of this rail member 70 sandwiched between the sliders 68 and 69. A columnar support portion 72 configured to abut on the skin of the pubic symphysis is attached to a lower portion of this slider 71.

Each of the rail members 61, 66, 67, and 70 is constituted of the two metal rods and the slider 71 having the columnar support portion 72 formed thereon is provided with respect to the rail member 61 through the two rail members 66 and 67 and the rail member 70 in order to assure flatness of the base jig BS and rigidity for torsion.

When the slider members 62 and 63 are moved along the rail member 61, the columnar support portions 64 and 65 can be installed in accordance with an interval between the left and right anterior superior iliac spines of the patient.

Moreover, when the sliders 68 and 69 are moved along the rail members 66 and 67 with respect to the rail member 61, the columnar support portion 72 on the lower portion of the slider 71 can be installed in accordance with a distance from a line connecting the left and right anterior superior iliac spine to the pubic symphysis of the patient.

Additionally, since the slider 71 can be moved along the rail member 70, even if the patient's pubic symphysis is not placed on a perpendicular line extending downwards from an intermediate position between the columnar support portions 64 and 65 and a position of the pubic symphysis deviates to either the left side or the right side, an end of the columnar support portion 72 can accurately abut on the skin surface on the pubic symphysis (through the attachment).

An operation during an actual surgical treatment will now be described for reference.

(1) The base jig BS subjected to interval adjustment in advance is installed based on the left and right anterior superior iliac spines and the pubic symphysis region of the patient.

(2) Pins are inserted to the left and right anterior superior iliac spines to fix the base jig BS.

(3) The attachment at the end of the columnar support on the distal side is fixed on the pubic symphysis using an adhesive tape.

(4) The direction indicating jig DI is disposed to the base jig BS, and the parameters a and) obtained by the preoperative simulation are used to install the direction indicating rod 43 parallel to the acetabular normal vector.

(5) A rod of an acetabular reamer configured to ream the acetabulum is held in such a manner that it becomes parallel to the direction indicating rod 43 of the direction indicating jig DI installed at (4), and reaming of the acetabulum is carried out.

(5-1) To hold the rod of the acetabular reamer parallel to the direction indicating rod 43 of the direction indicating jig DI, a holding device of the reamer can be additionally mechanically prepared to mechanically support a surgeon who is an operator.

(5-2) Further, the direction indicating jig DI may be constituted of or used with an optical tool such as a laser pointer, and a mechanical holding device of the acetabular reamer can be thereby used in cooperation with a computer to provide digital control.

(5-3) Furthermore, a range finder configured to measure an acetabular insertion depth can be provided to the direction indicating jig DI to perform reaming so that a scale mark provided on the reamer rod can move a length for a corresponding depth. In this case, the range finder can be used in cooperation with such a mechanical device as described in (5-2) to provide digital control.

As described above, according to this embodiment, an individual difference of a patient can be appropriately reflected to accurately determine a reaming operation for a pelvic acetabulum before a preoperative treatment, and an operation accurately reproducing contents determined before the preoperative treatment can be carried out during the surgical treatment.

It is to be noted that the present invention is not restricted to the configurations of the base jig BS and the direction indicating jig DI described in the foregoing embodiment.

It is to be noted that the base jig may be referred to as a "device" in this specification. Moreover, the direction indicating rod of the direction indicating jig may be referred to as an "indicator".

<Example of Base Jig>

Figure 25:
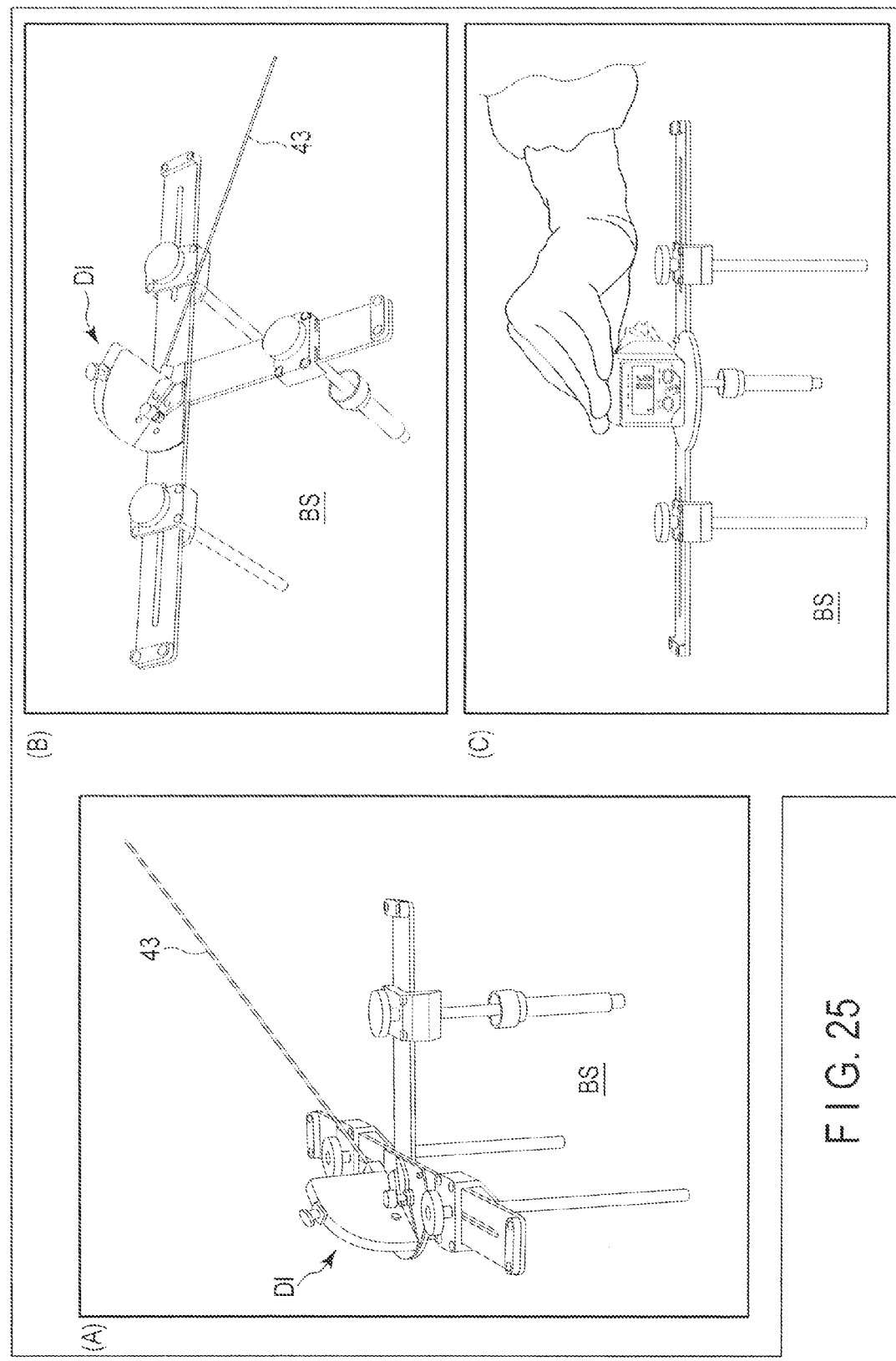
FIG. 25 is a view showing the appearance configuration of the base jig according to the embodiment.

In the description associated with FIG. 20 to FIG. 24, the example of the base jig BS (and the direction indicating jig DI with the direction indicating rod 43 disposed to the base jig) has been given, but this jig may be specifically configured as shown in, e.g., FIG. 25. In this case, preoperative planning premised on use of the base jig BS is performed even in a preoperative planning program.

FIG. 25 (A) is a perspective view showing an example of the base jig BS. FIG. 25 (B) is a perspective view showing the example of the base jig BS from another direction. FIG. 25 (C) is a view showing a state that a level gauge is used to perform adjustment so that a surface (a jig plane) of a frame body of the direction indicating jig DI becomes level by changing a length of the columnar support of the base jig BS (the columnar support that abuts on the body surface on the pubic symphysis).

It is to be noted that the direction indicating jig DI can be disposed to an arbitrary position on the surface of the frame body. That is, the direction indicating jig DI is not restricted to an example where it is disposed to a position near an upper end of the columnar support abutting on the body surface on the left anterior superior iliac spine or the right anterior superior iliac spine, and it may be disposed to a position near an intermediate point of a line connecting upper ends of the respective columnar supports abutting on the body surface on the left and right anterior superior iliac spines as shown in FIG. 25. The direction indicating rod 43 is used to reproduce the direction parallel to the acetabular normal vector as described above.

<Example of Measurement of Soft Tissue Thickness>

Figure 26:
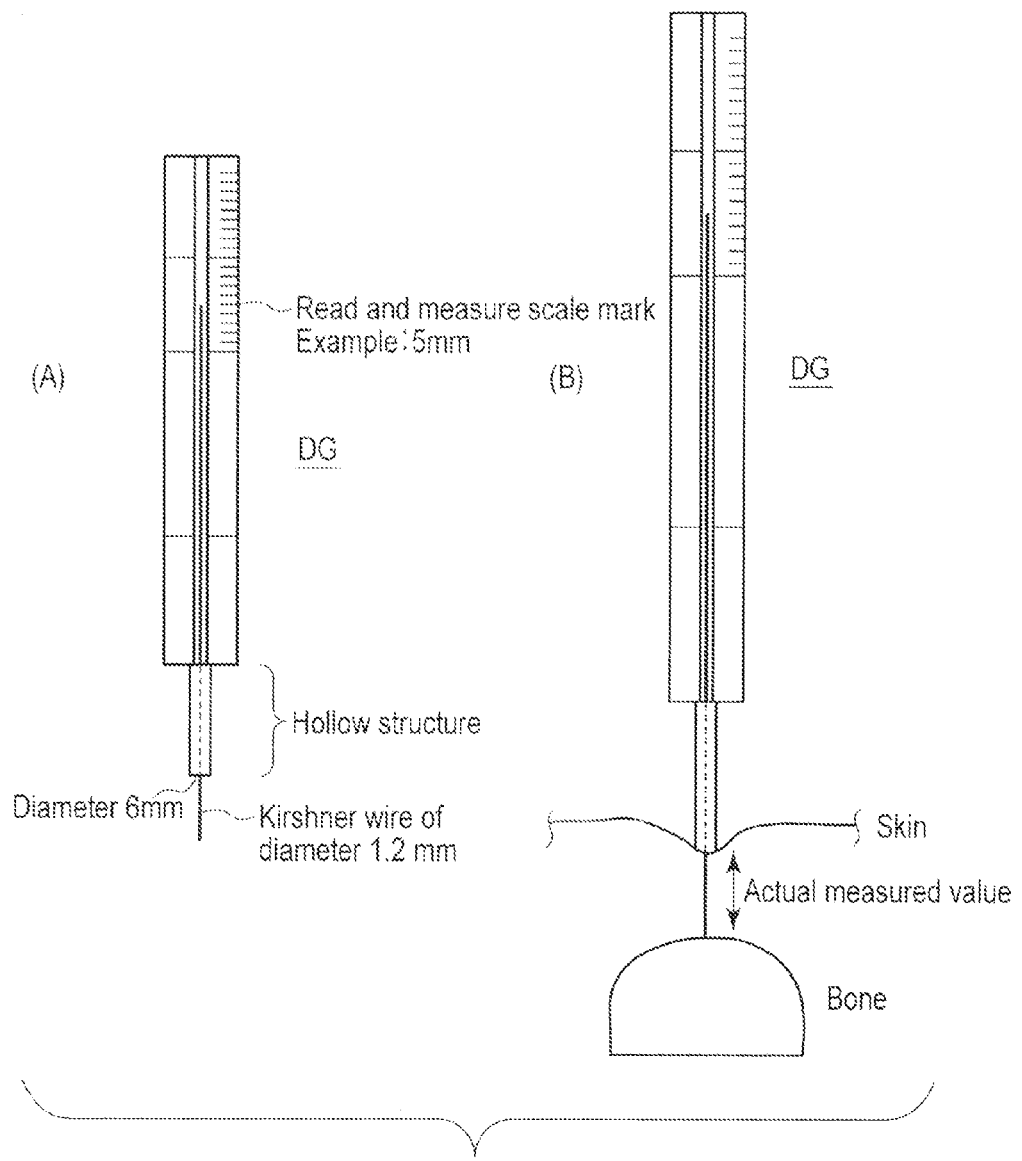
FIG. 26 is a view showing a configuration of a depth gauge according to the embodiment.

In steps S110 to S113 in FIG. 2, FIG. 15 to FIG. 17, and the associated description, the procedure for calculating a distance between each of the left and right anterior superior iliac spines and the skin surface and a distance between the pubic symphysis and the skin surface (a soft tissue thickness) has been explained, these distance may be measured using, e.g., a depth gauge DG shown in FIG. 26 to increase an accuracy, and values obtained by this actual measurement may be taken into consideration to set a three-dimensional image of the base jig.

As shown in FIG. 26 (A), the depth gauge DG is provided with scale marks indicating a protruding length of a Kirschner wire from a hollow structure end portion. At the time of use, as shown in FIG. 26 (B), in a state that the hollow structure end portion of the depth gauge DG is manually appressed against the skin, the Kirschner wire is inserted from the skin to reach the bone. As a result, a distance from the skin surface to the bone is indicated by the scale marks. It is to be noted that pressing force at this moment does not substantially irreversibly damage the skin, and it is equivalent to, e.g., force for actually pressing each columnar support portion of the base jig BS.

Errors can be reduced and an accuracy can be improved by using actual measured values obtained by measuring the soft tissue thickness using the depth gauge DG in this manner to set a three-dimensional image of the base jig. Further, the soft tissue thickness can be accurately obtained at a low cost as compared with a method for performing CT imaging to obtain the soft tissue thickness.

<Countermeasure for Error Due to Difference in Soft Tissue Thickness>

Figure 27:
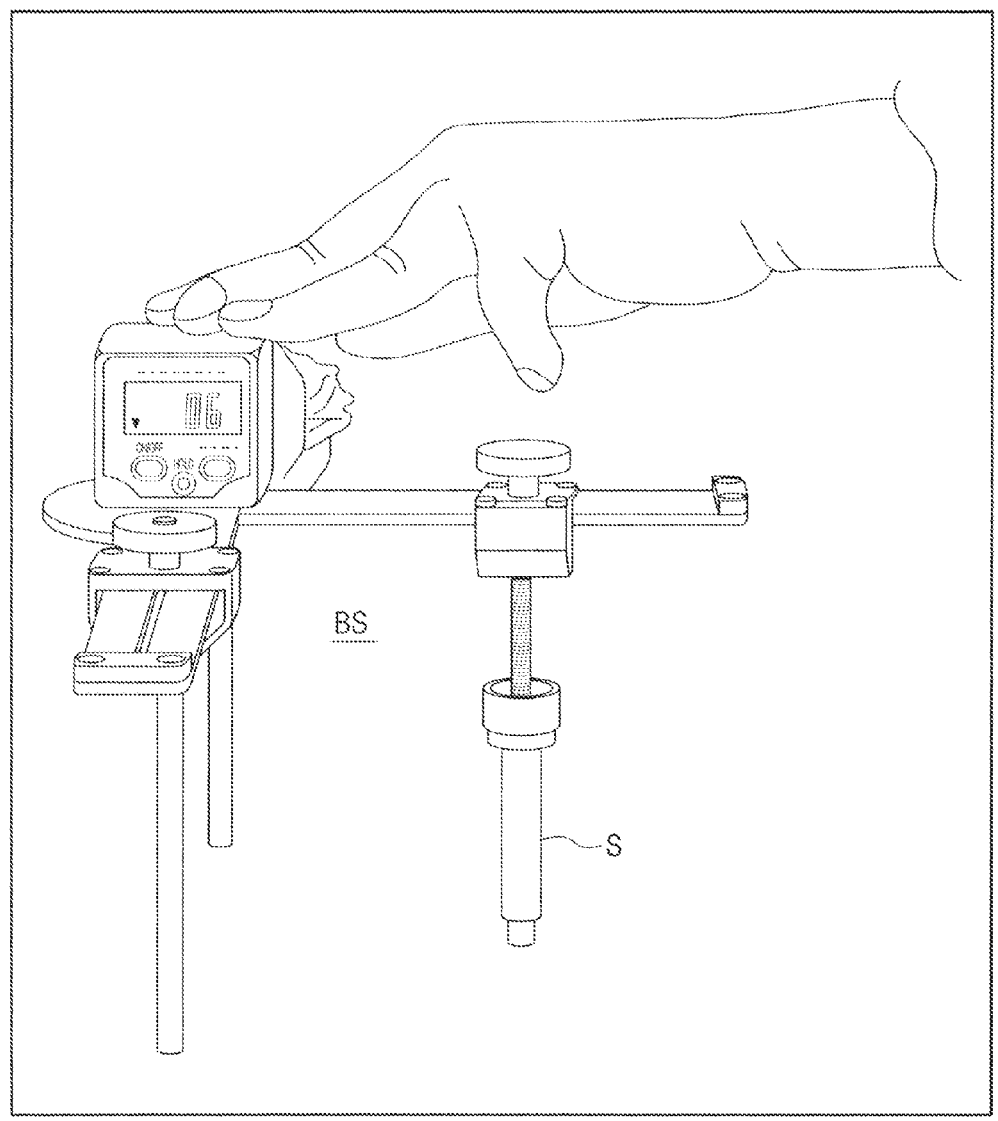
FIG. 27 is a view showing the appearance configuration of the base jig according to the embodiment.

As shown in FIG. 27, the base jig BS has a columnar support S (a columnar support abutting on the body surface on the pubic symphysis) whose axial length can be changed when rotated, and an inclination of the surface (the jig plane) of the frame body of the direction indicating jig DI can be changed by varying the length of this columnar support S. Here, the surface of the frame body becomes level by equalizing lengths of the three columnar supports of the direction indicating jig DI.

Figure 28:
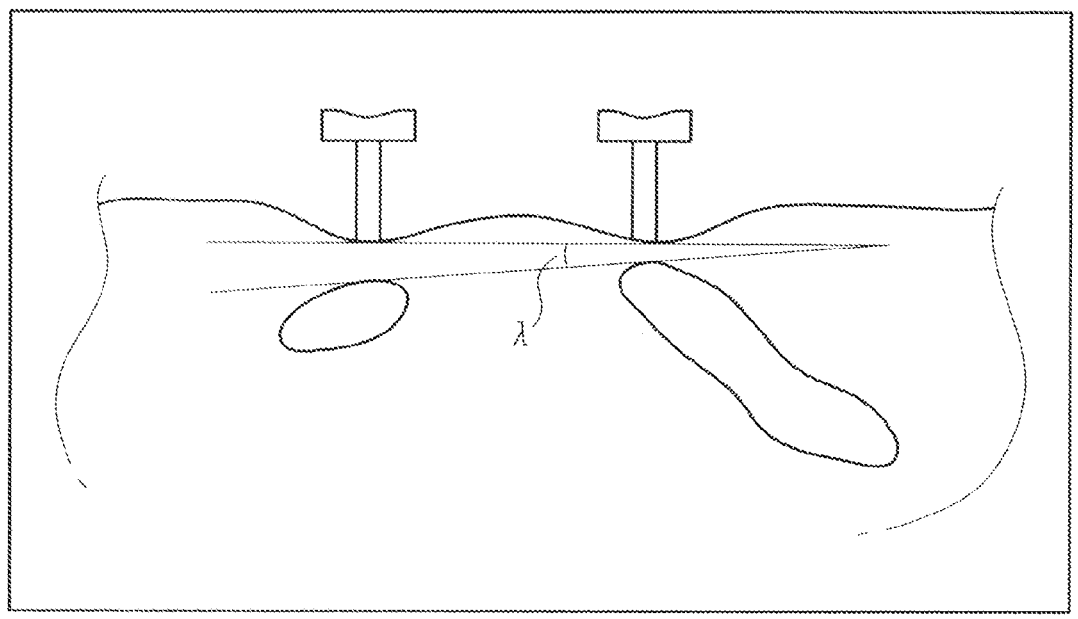
FIG. 28 is a view showing an error with respect to an APP plane according to the embodiment.

Meanwhile, although the jig plane of the direction indicating jig DI reproduces the APP plane (the plane formed of a triangle connecting three points, i.e., the left and right anterior superior iliac spines LM11 and LM12 and the pubic symphysis LM13 in FIG. 7), since a thickness of the soft tissue (an ASIS soft part thickness) on each of the left and right anterior superior iliac spines abutting on the columnar supports is different from a thickness of the soft tissue (a pubic region soft part thickness) on the pubic symphysis, errors may be observed in a three-dimensional image of the base jig BS unless any countermeasure is taken. For example, as shown in FIG. 28, an angle $\lambda$ is produced between the APP plane that is in contact with the left and right anterior superior iliac spines and the pubic symphysis and the plane that is in contact with the ends of the respective columnar supports.

There are the following two countermeasures for this problem.

(i) In a three-dimensional image of the base jig BS, the length of the columnar support S (the support abutting on the body surface on the pubic symphysis) is corrected so that the jig plane becomes parallel to the APP plane. That is, the jig plane is inclined to offset the angle $\lambda$.

(ii) In the three-dimensional image of the base jig, a direction of the direction indicating rod 43 is corrected in accordance with the angle $\lambda$ while maintaining the same length for the respective columnar supports. That is, an angle of the direction indicating rod 43 (an angle of the cup normal vector) based on the jig plane is calculated. A specific calculation method in this case will now be described hereinafter.

Definition of OA, RA, RI, and OI

Figure 29:
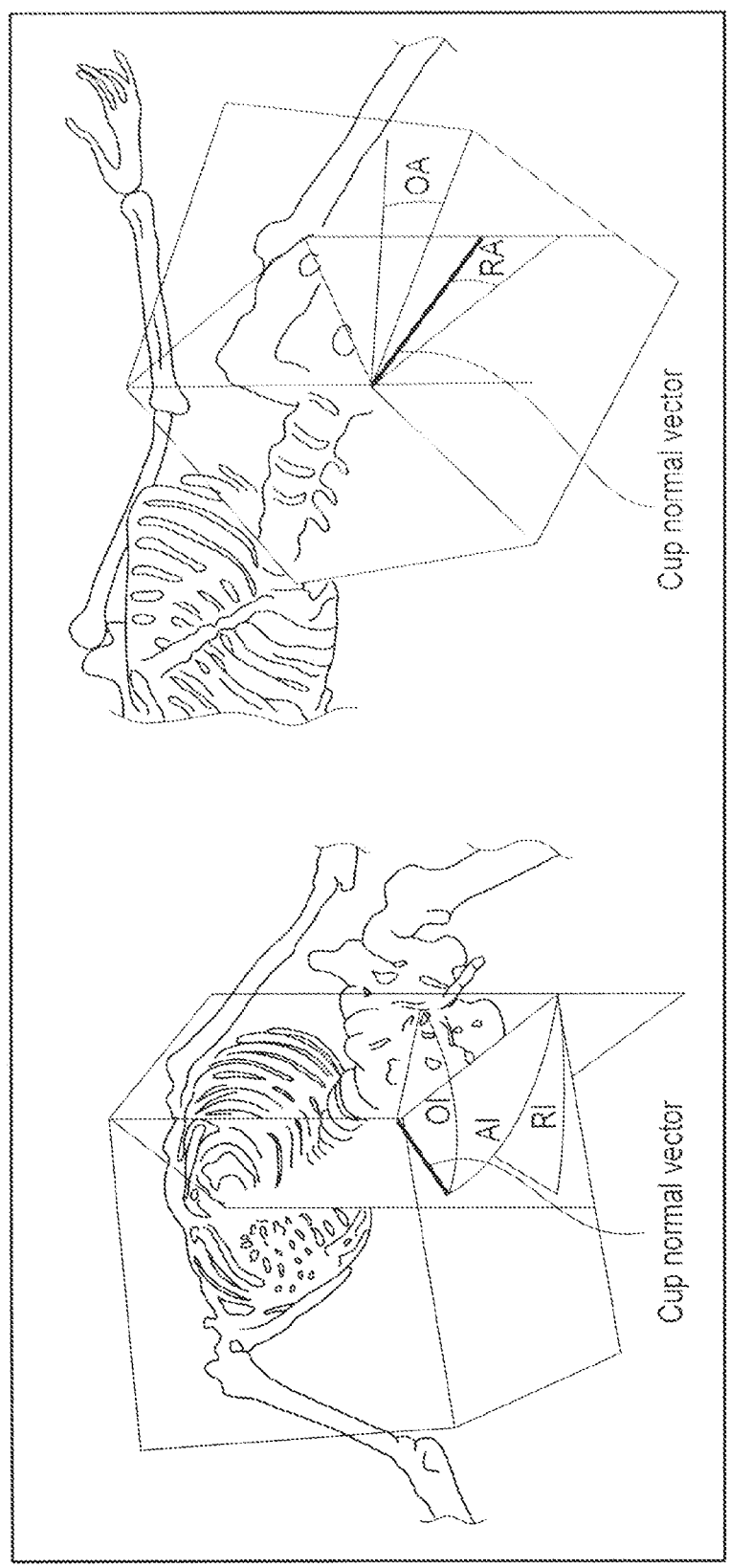
FIG. 29 is a view showing a definition of a cup normal vector according to the embodiment.
Figure 30:
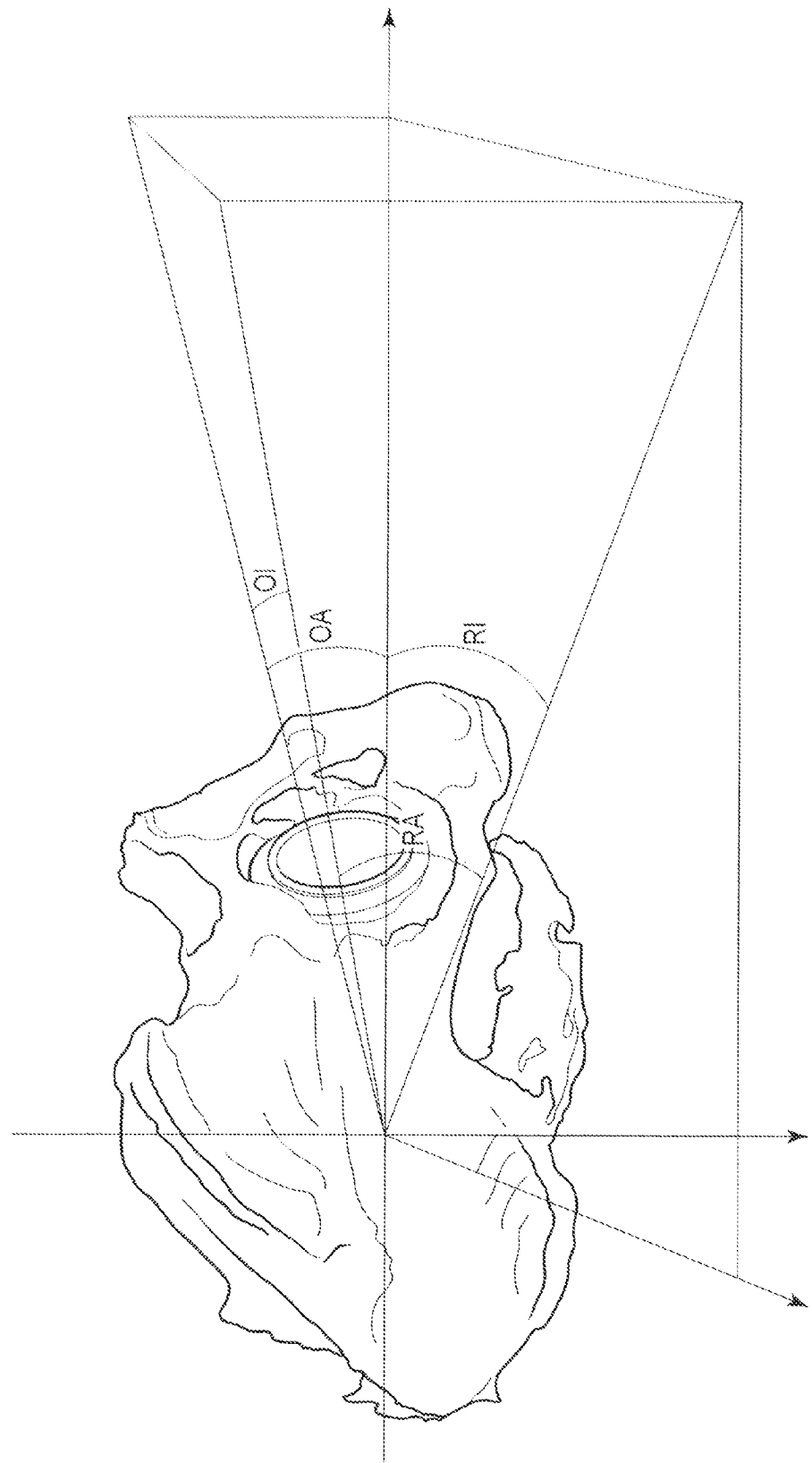
FIG. 30 is a view showing the definition of the cup normal vector according to the embodiment.

In the operative field, angles OA, RA, RI, and OI formed by the cup normal vector are defined as shown in FIG. 29 and FIG. 30. A coordinate system in this case corresponds to the coordinate system of the pelvis PV depicted in FIG. 7. In this case, the following relationships can be achieved.

$$\tan(OA) = \tan(RA) \times \cos(RI) \quad (1)$$

$$\sin(OI) = \sin(RI) \times \cos(RA) \quad (2)$$

When these representations are deformed, RA and OI can be expressed as follows, respectively.

$$RA = \tan^{-1}\{\tan(OA)/\cos(RI)\} \quad (3)$$

$$OI = \sin^{-1}\{\sin(RI) \times \cos(RA)\} \quad (4)$$

Correction when Jig Plane (APP') is Inclined in Saggital Sectional Direction with Respect to APP When the jig plane (APP') is inclined the angle $\lambda$ in the saggital sectional direction with respect the APP, angles OA', RA', and RI' from the jig plane (APP') with respect to the plan values OA, RA, and RI can be expressed as follows, respectively.

$$OA' = OA + \lambda \quad (5)$$

where, $\tan\lambda = \{(\text{pubic region soft part thickness}) - (\text{ASIS soft part thickness})\}/(\text{pelvic height})$ It is to be noted that the pelvic height means a distance from a line connecting the left and right anterior superior iliac spines (a tangent line of both ASIS) to the pubic symphysis LM13 depicted in FIG. 7.

$$RI' = \tan^{-1}\{\tan(OI')/\cos(OA')\} \quad (6)$$
$$= \tan^{-1}[\tan(OI)/\cos\{(OA') + \lambda\}]$$
$$= \tan^{-1}[\tan[\sin^{-1}\{\sin(RI) \times \cos(RA)\}/\cos\{OA + \lambda\}]]$$

$$RA' = \tan^{-1}\{\tan(OA')/\cos(RI')\} \quad (7)$$
$$= \tan^{-1}\left[\frac{\tan\{(OA) + \lambda\} \times}{\cos[\tan^{-1}[\tan[\sin^{-1}\{\sin(RI) \times \cos(RA)\}/\cos\{OA + \lambda\}]]]}\right]$$

It is to be noted that a modification of Expression (6) uses a fact that OI-OI' can be achieved and also uses Expression (5) and Expression (4).

Further, a modification of Expression (7) uses Expression (5) and Expression (6).

Therefore, using Expressions (5) to (7) enables calculating the plan values based on the jig plane.

<Validation of Accuracy of Base Jig>

Figure 31:
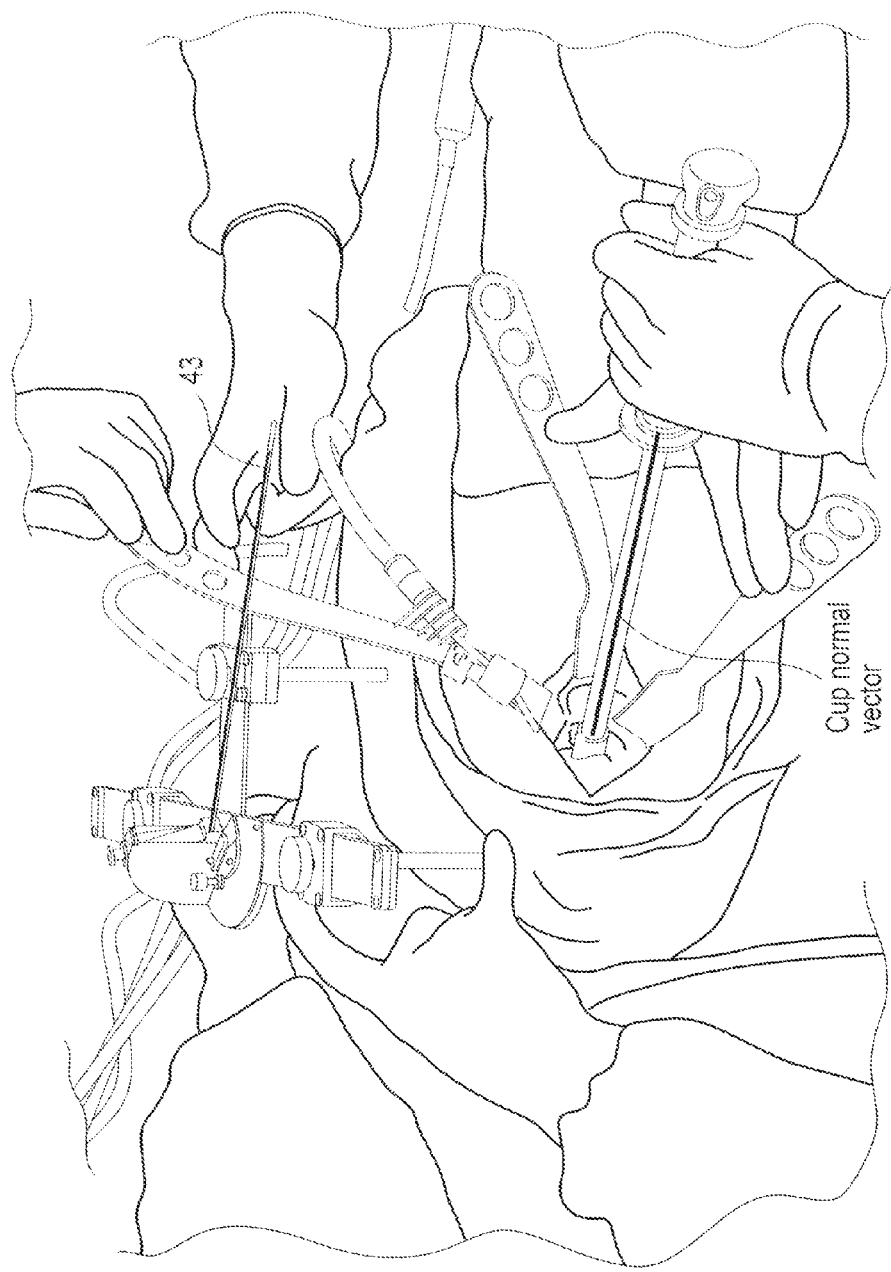
FIG. 31 is a view showing how an acetabular cup is implanted according to the embodiment.

FIG. 31 is a view showing a state that the acetabular cup CP is implanted by a cup holder into the pelvis parallel to the direction of the direction indicating rod (the indicator) 43 provided to the base jig (the device) BS after performing the preoperative plan.

A method of validating an accuracy of the base jig BS used in this example will now be described hereinafter.

The accuracy of the base jig BS is validated by calculating an error of an anteversion angle RA and an error of an inclination angle RI excluding manual errors, respectively.

<Validation of Accuracy of Anteversion Angle RA>

In validation of an accuracy of the anteversion angle RA of the base jig BS, a difference between an anteversion angle from a horizontal plane of the direction indicating rod (the indicator) 43 and an anteversion angle from a horizontal plane of a normal vector of the acetabular cup CP installed in the pelvic acetabulum (a normal vector indicated by the cup holder) is first actually measured in the operative field, and then a difference between an anteversion angle of the normal line of the acetabular cup CP in the preoperative planning and a value obtained by subtracting the above-described difference from the anteversion angle of the normal line of the acetabular cup CP imaged after postoperative CT imaging is obtained.

This calculation can be represented by Expressions as follows.

Intraoperative compromise error $RA$=(anteversion angle from horizontal plane of indicator of device)−(anteversion angle from horizontal plane of cup holder) (8)

$RA$ error of Device=preoperative plan $RA$−{(postoperative $CT$ $RA$)−(intraoperative compromise error $RA$)} (9)

It is to be noted that the postoperative CT RA represents the anteversion angle RA acquired from the postoperative CT imaging.

Furthermore, the intraoperative compromise error RA represents a procedural anteversion angle RA error during the operation which should be eliminated from pure errors of the device.

<Validation of Accuracy of Inclination Angle RI>

In validation of an accuracy of the inclination angle RI of the base jig BS, a line parallel to the direction indicating rod (the indicator) 43 and a normal line of the acetabular cup CP installed in the pelvic acetabulum are first projected onto the horizontal plane, arbitrary two points are provided on each of the two projected lines, an angle θ formed by the two lines is obtained based on lengths of sides and inner angles of two triangles formed of a total of four points, an angle θ' formed of the two lines on the jig plane is then obtained based on the angle θ, and finally a difference between an inclination angle of the normal line of the acetabular cup CP at the time of the preoperative planning and a value obtained by subtracting the angle θ' from the inclination angle of the normal line of the acetabular cup CP imaged after the surgical treatment is calculated.

A specific method is as follows.

Figure 32:
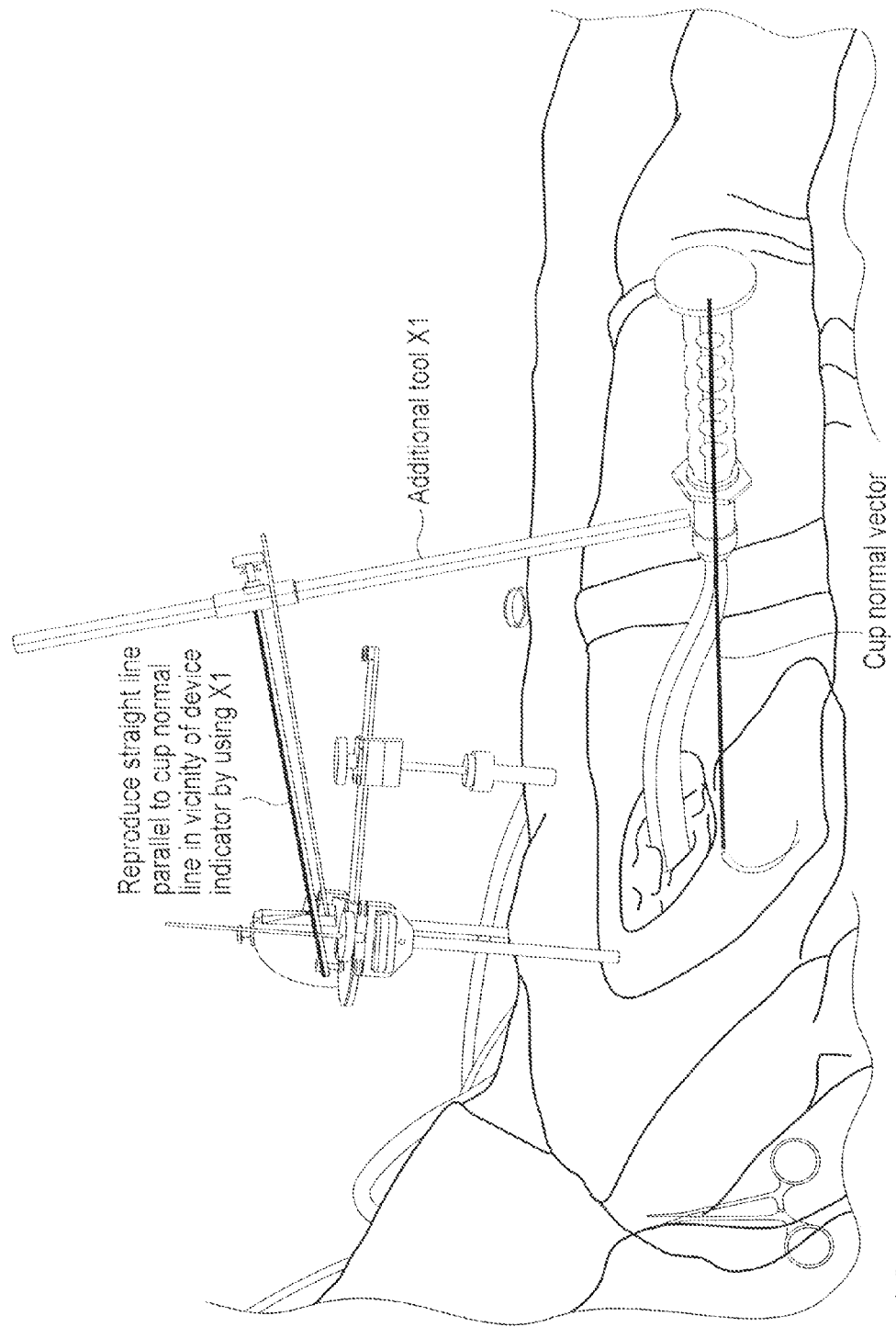
FIG. 32 is a view showing installation of an additional tool according to the embodiment.

First, as shown in FIG. 32, an additional tool X1 is used to reproduce a line parallel to the cup normal vector in the vicinity of the direction indicating rod (the indicator) 43.

Figure 33:
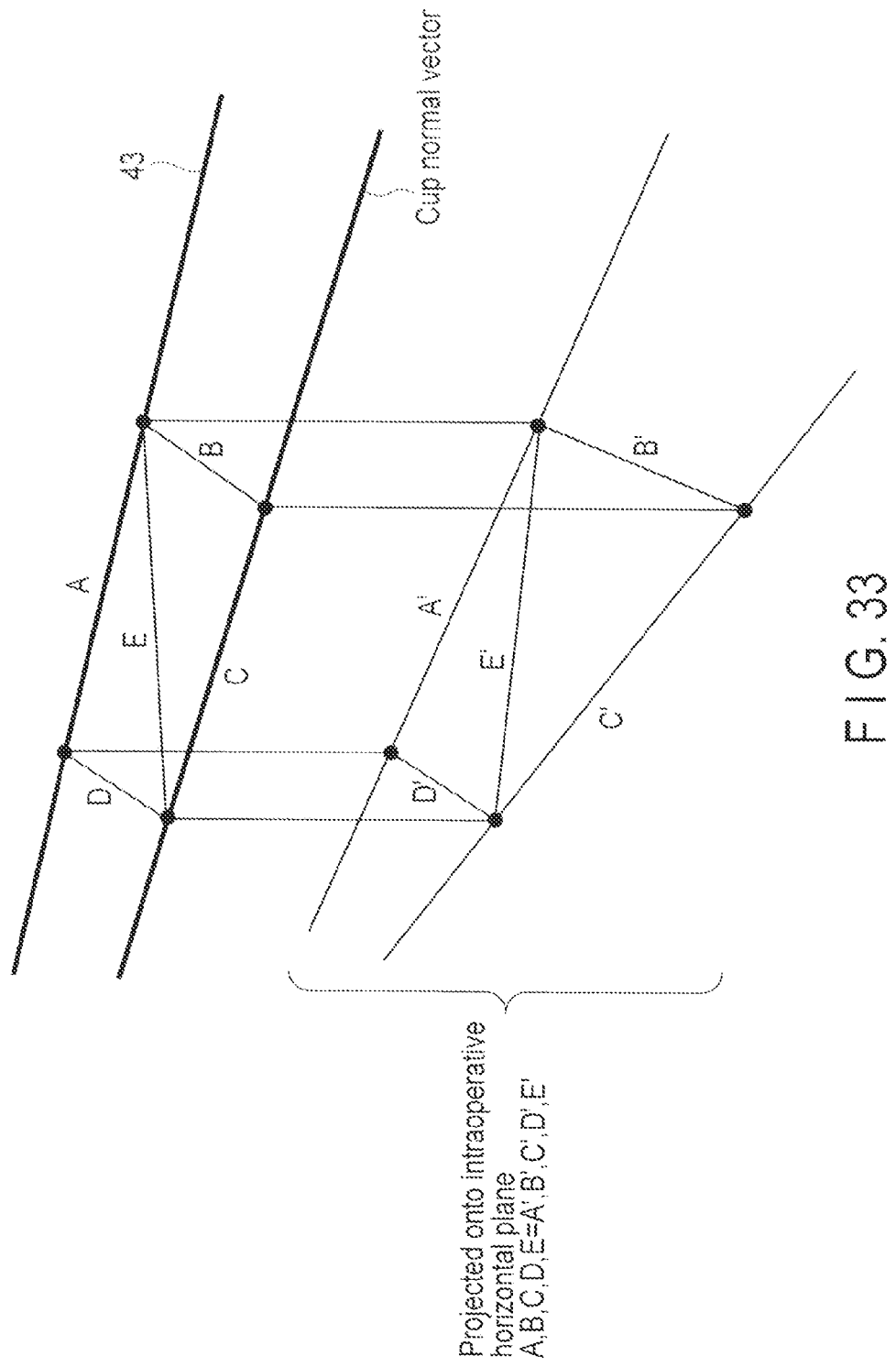
FIG. 33 is a view showing a process of validating an accuracy of the base jig according to the embodiment.

Then, as shown in FIG. 33, a total of four points are provided, namely, two points are provided on the straight line of the direction indicating rod (the indicator) 43, and two points are provided on the straight line parallel to the cup holder reproduced using the additional tool X1, and a square ABCD and a diagonal line E are provided.

Figure 34:
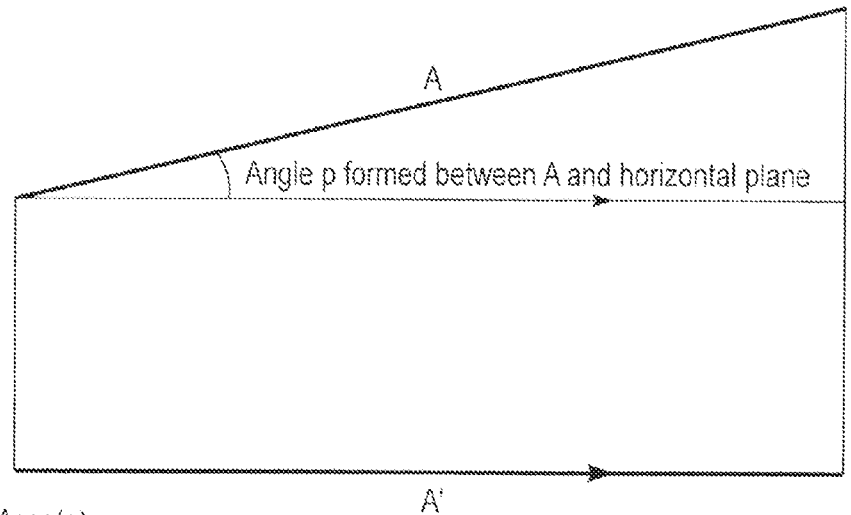
FIG. 34 is a view showing the process of validating the accuracy of the base jig according to the embodiment.

Then, as shown in FIG. 34, lengths of the sides A, B, C, D, and E and angles p, q, r, s, and t that become horizontal during the surgical treatment are measured, respectively.

Assuming that sides A', B', C', D', and E' are obtained by projecting the sides A, B, C, D, and E onto an intraoperative horizontal plane, lengths of the respective sides are as follows.

$$A' = A \cdot \cos(p) \quad (10)$$

$$B' = B \cdot \cos(q) \quad (11)$$

$$C' = C \cdot \cos(r) \quad (12)$$

$$D' = D \cdot \cos(s) \quad (13)$$

$$E' = E \cdot \cos(t) \quad (14)$$

Figure 35:
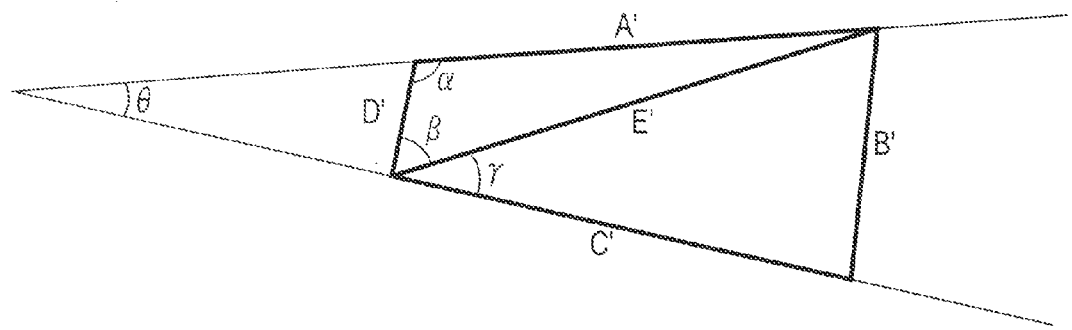
FIG. 35 is a view showing the process of validating the accuracy of the base jig according to the embodiment.

As shown in FIG. 35, when α, β, and γ are assured with respect to a square A'B'C'D' and a diagonal line E' and θ is an angle formed by A' and C', the following relationship is achieved.

$$\theta = (\alpha + \beta + \gamma) - 180° \quad (15)$$

Furthermore, α, β, and γ can be represented as follows based on the law of cosines.

$$\alpha = \cos^{-1}[\{(A')^2 + (D')^2 - (E')^2\}/2A'D'] \quad (16)$$

$$\beta = \cos^{-1}[\{(D')^2 + (E')^2 - (A')^2\}/2D'E']. \quad (17)$$

$$\gamma = \cos^{-1}[\{(C')^2 + (E')^2 - (B')^2\}/2C'E'] \quad (18)$$

Using these angles enables representing 9 as follows.

$$\theta \cos^{-1}[\{(A')^2+(D')^2-(E')^2\}/2A'D']+\cos^{-1}[\{(D')^2+(E')^2-(A')^2\}/2D'E']+\cos^{-1}[\{(C')^2+(E')^2-(B')^2\}/2C'E']-180° \quad (19)$$

In this manner, θ can be calculated.

Subsequently, as shown in FIG. 36, (APP) is determined as an angle formed between the APP plane and the horizontal plane, θ' is determined as an inclination angle error on the APP plane, and (RI') is determined as a preoperative planning inclination angle projected onto the horizontal plane. Relationships l=l'−·cos(APP), m=m', and n=n' are achieved between the APP plane and the horizontal plane.

At this time, θ' can be calculated based on the following expressions.

$$\tan(RI') = \{\sin(RI)/\cos(RI) \cdot \cos(APP)\} \quad (20)$$
$$= \tan(RI)/\cos(APP)$$

$$RI' = \tan^{-1}\{\tan(RI)/\cos(APP)\} \quad (21)$$

Likewise, $$\tan(RI' + \theta) = \tan(RI + \theta')/\cos(APP) \quad (22)$$

$$\tan(RI + \theta') = \tan(RI' + \theta) \cdot \cos(APP) \quad (23)$$

$$RI + \theta' = \tan^{-1}\{\tan(RI' + \theta) \cdot \cos(APP)\} \quad (24)$$

$$\theta' = \tan^{-1}\{\tan(RI' + \theta) \cdot \cos(APP)\} - RI \quad (25)$$

$$= [[\tan^{-1}\{\tan(RI)/\cos(APP)\} + \theta] \cdot \cos(APP)] - RI \quad (26)$$

Therefore, an error of the inclination angle RI can be obtained based on the following expression.

Error of the inclination angle RI of the device=Preoperative planning RI−{(postoperative CT RI)−θ} (27)

Since a pure device error excluding manual errors can be calculated in this manner, an accuracy of the device can be appropriately validated.

Figure 37:
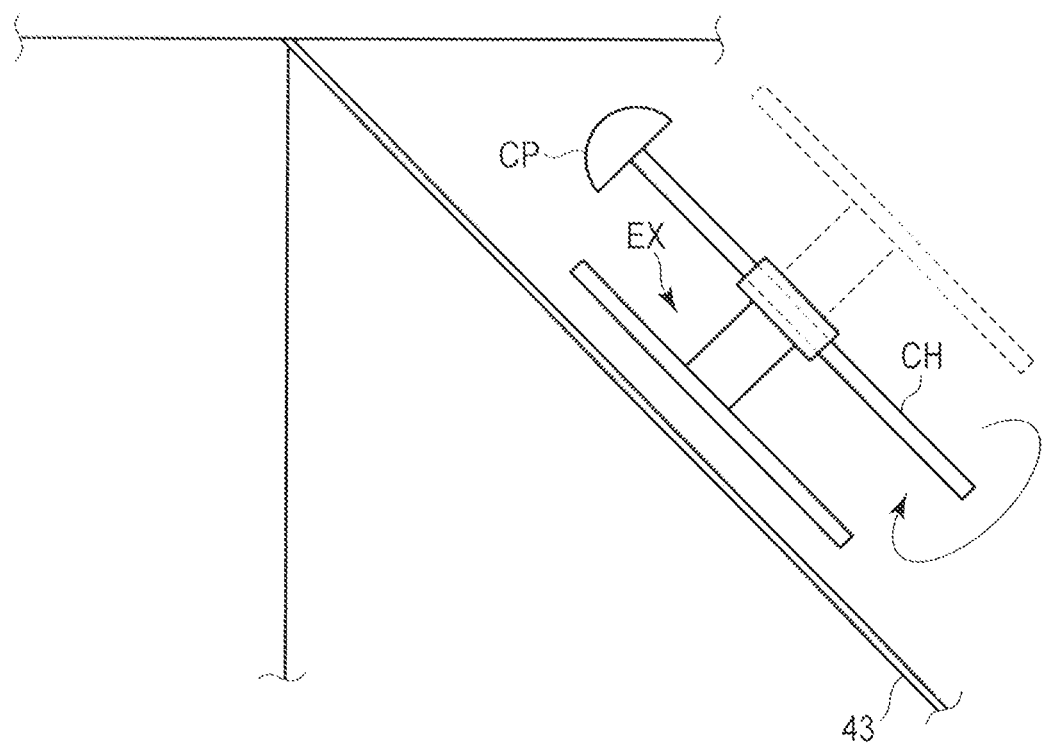
FIG. 37 is a view showing a modification of validating the accuracy of the base jig according to the embodiment.

It is to be noted that, although FIG. 32 illustrates the situation that the straight line parallel to the cup normal vector is reproduced in the vicinity of the direction indicating rod (the indicator) 43 using the additional tool X1, the method of reproducing the straight line is not restricted thereto. Alternatively, as shown in FIG. 37, an extension rod EX may be rotatably disposed to the cup holder CH, and this rod EX may be used to reproduce the straight line parallel to the cup normal vector in the vicinity of the direction indicating rod (the indicator) 43. In this case, the same effect as that of the configuration depicted in FIG. 32 can be obtained. Additionally, when implanting the acetabular cup CP into the pelvis using the cup holder CH, the implantation can be consciously performed so that the direction indicating rod (the indicator) 43 can become parallel to the rod EX placed near this rod, thereby increasing the accuracy at the time of the implantation.

Besides, the present invention is not restricted to the foregoing embodiment, and it can be modified in many ways without departing from the gist at the embodying stage. Further, the functions executed in the foregoing embodiment can be appropriately combined to be carried out as much as possible. The foregoing embodiment includes various stages, and various inventions can be extracted by appropriately combining disclosed constituent elements. For example, even if some of all constituent elements disclosed in the embodiment are eliminated, a configuration having these constituent elements eliminated can be extracted as an invention as long as effects can be obtained.

As described above in detail, according to the present invention, an individual difference of a patient can be appropriately reflected before a surgical treatment to accurately determine a reaming operation of the pelvic acetabulum, and the operation accurately reproducing contents determined before the surgical treatment can be carried out during the surgical treatment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A preoperative planning method performed by a computer for hip replacement arthroplasty, the method comprising:
   an image input step of inputting two-dimensional tomographic images of a patient's lower extremities including a pelvis and a femur;
   an image reconstruction step of reconstructing a three-dimensional image of the patient's lower extremities including the pelvis and the femur from the two-dimensional tomographic images input at the image input step;
   a joint prostheses determination step of determining installation positions and installation directions of joint prostheses which are installed in a pelvic acetabulum from the three-dimensional image obtained at the image reconstruction step;
   a base jig setting step of setting a three-dimensional image of a base jig having three or more columnar supports which abut on three or more reference points of the pelvis with respect to the three-dimensional image obtained at the image reconstruction step; and
   a parameter acquisition step of acquiring a direction of an indicator which runs through a predetermined position on the base jig in the three-dimensional image of the base jig set at the base jig setting step and becomes parallel to the installation direction of the joint prostheses determined at the joint prostheses determination step.

2. The preoperative planning method according to claim 1, wherein:
   at the base jig setting step, the three-dimensional image of the base jig having three columnar supports using three points, which correspond to left and right anterior superior iliac spines and a pubic symphysis of the pelvis, as the reference points, is set, and
   at the parameter acquisition step, the direction of the indicator which runs through the vicinity of an upper end of the columnar support abutting on a body surface on the left anterior superior iliac spine or the right anterior superior iliac spine or the vicinity of an intermediate point of a line connecting upper ends of the respective columnar supports abutting on the body surface on the left and right anterior superior iliac spines in the three-dimensional image of the base jig is parameterized and acquired in the three-dimensional image of the base jig.

3. The preoperative planning method according to claim 1, wherein, at the base jig setting step, the three-dimensional image of the base jig is set while considering a distance between the pelvis and the skin surface with respect to the three-dimensional image of the pelvis obtained at the image reconstruction step.

4. The preoperative planning method according to claim 3, wherein the distance between the pelvis and the skin surface is an actual measurement value obtained by measurement using a depth gauge.

5. The preoperative planning method according to claim 1, wherein, at the base jig setting step, a length of at least one columnar support is corrected in accordance with a difference in distance between the pelvis and the skin surface at each reference point such that a plane supported by the respective columnar supports becomes parallel to a plane including the respective reference points of the pelvis in the three-dimensional image of the base jig.

6. The preoperative planning method according to claim 1, wherein, at the base jig setting step, the direction of the indicator is corrected in accordance with a difference in distance between the pelvis and the skin distance at each reference point while maintaining the same length for the respective columnar supports three-dimensional image of the base jig.

7. An operation support jig, comprising:
   a base jig including three or more columnar supports whose intervals are adjustable with respect to a frame body forming one plane; and
   a direction indicating jig which is disposed at a predetermined position on a surface of the frame body and includes an indicator which indicates the direction acquired at the parameter acquisition step in the preoperative planning method according to claim 1.

8. The operation support jig according to claim 7, wherein:
   the base jig includes three columnar supports abutting on three points which correspond to left and right anterior superior iliac spines and a pubic symphysis of a pelvis, and
   the direction indicating jig is disposed in the vicinity of an upper end of the columnar support abutting on a body surface of the left anterior superior iliac spine or the right anterior superior iliac spine or the vicinity of an intermediate point of a line connecting upper ends of the respective columnar supports abutting on the body surface of the left and right anterior superior iliac spines.

9. The operation support jig according to claim 8, wherein each of the ends of the two columnar supports of the base jig abutting or the left and right anterior superior iliac spines of the pelvic includes a fixing member that is fixed to each anterior superior iliac spine.

10. An accuracy validation method performed by a computer for an operation support jig comprising a base jig including three or more columnar supports whose intervals are adjustable with respect to a frame body forming one plane and a direction indicating jig which is disposed at a predetermined position on a surface of the frame body and includes an indicator which indicates an arbitrary direction and angle based on a plane of the frame body, the method comprising:
   obtaining a difference between an anteversion angle from a horizontal plane of the indicator and an anteversion angle from a horizontal plane of a normal line of an acetabular cup installed in a pelvic acetabulum; and
   obtaining a difference between the anteversion angle of the normal line of the acetabular cup at the time of preoperative planning and a value obtained by subtracting the difference from the anteversion angle of the normal line of the acetabular cup imaged after a surgical treatment.

11. An accuracy validation method performed by a computer for an operation support jig comprising a base jig including three or more columnar supports whose intervals are adjustable with respect to a frame body forming one plane and a direction indicating jig which is disposed at a predetermined position on a surface of the frame body and includes an indicator which indicates an arbitrary direction and angle based on a plane of the frame body, the method comprising:
   projecting a line parallel to the indicator and a normal line of an acetabular cup installed in a pelvic acetabulum onto a horizontal plane, providing arbitrary two points on each of the two projected lines, and obtaining a first angle formed between the two lines based on lengths of sides and inner angles of two triangles formed of a total of four points;
   obtaining a second angle formed between the two lines on a plane of the frame body based on the first angle; and
   obtaining a difference between an inclination angle of the normal line of the acetabular cup at the time of preoperative planning and a value obtained by subtracting the second angle from the inclination angle of the normal line of the acetabular cup imaged after a surgical treatment.

* * * * *